(12) United States Patent
Nitzan et al.

(10) Patent No.: US 11,166,730 B2
(45) Date of Patent: Nov. 9, 2021

(54) SYSTEMS AND METHODS FOR REDUCING PRESSURE AT AN OUTFLOW OF A DUCT

(71) Applicant: White Swell Medical Ltd, Kibbutz Shefayim (IL)

(72) Inventors: Yaacov Nitzan, Hertzelia (IL); Menashe Yacoby, Ramat Gan (IL); Tanhum Feld, Merhavya (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 122 days.

(21) Appl. No.: 16/373,175

(22) Filed: Apr. 2, 2019

(65) Prior Publication Data
US 2019/0223877 A1 Jul. 25, 2019

Related U.S. Application Data

(63) Continuation of application No. 15/867,003, filed on Jan. 10, 2018, now Pat. No. 10,285,708, which is a (Continued)

(51) Int. Cl.
*A61M 31/00* (2006.01)
*A61M 37/00* (2006.01)
(Continued)

(52) U.S. Cl.
CPC .. *A61B 17/12109* (2013.01); *A61B 17/12036* (2013.01); *A61B 17/12045* (2013.01);
(Continued)

(58) Field of Classification Search
CPC ........ A61B 17/12036; A61B 17/12045; A61B 17/12109; A61B 17/12136; A61M 1/122;
(Continued)

(56) References Cited

U.S. PATENT DOCUMENTS 3,211,150 A   10/1965 Foderick
3,926,175 A   12/1975 Allen et al.
(Continued)

FOREIGN PATENT DOCUMENTS

EP   0526102 A1   2/1993
EP   2353501 A1   8/2011
(Continued)

OTHER PUBLICATIONS

International Search Report and Written Opinion dated Apr. 12, 2018, for PCT/IB17/01488, filed Oct. 31, 2017 (11 pages).
(Continued)

*Primary Examiner* — Rebecca E Eisenberg
(74) *Attorney, Agent, or Firm* — Brown Rudnick LLP

(57) ABSTRACT

Various systems and methods are provided for reducing pressure at an outflow of a duct such as the thoracic duct or the lymphatic duct. In one embodiment, an indwelling catheter can be configured to be at least partially implanted within a vein of a patient in the vicinity of an outflow port of a duct of the lymphatic system. The catheter can include first and second restrictors each configured to at least partially occlude the vein within which the catheter is implanted and thus to restrict fluid flow within the vein when the restrictors are activated. The restrictors can each be configured to move between an activated configuration, in which the restrictor occludes the vein, and a relaxed configuration, in which the restrictor does not occlude the vein. The catheter can include a pump, such as an axial motor pump, configured to pump fluid through the catheter.

15 Claims, 26 Drawing Sheets

Related U.S. Application Data continuation of application No. 15/150,637, filed on May 10, 2016, now Pat. No. 10,149,684.

(60) Provisional application No. 62/233,802, filed on Sep. 28, 2015, provisional application No. 62/159,465, filed on May 11, 2015.

(51) Int. Cl.
| | | |
|---|---|---|
| *A61B 17/12* | (2006.01) | |
| *A61M 60/40* | (2021.01) | |
| *A61M 60/50* | (2021.01) | |
| *A61M 60/135* | (2021.01) | |
| *A61M 60/148* | (2021.01) | |
| *A61M 60/205* | (2021.01) | |
| *A61M 60/414* | (2021.01) | |
| *A61M 60/833* | (2021.01) | |
| *A61M 60/857* | (2021.01) | |

(52) U.S. Cl.
CPC ..... *A61B 17/12136* (2013.01); *A61M 60/135* (2021.01); *A61M 60/148* (2021.01); *A61M 60/205* (2021.01); *A61M 60/40* (2021.01); *A61M 60/414* (2021.01); *A61M 60/50* (2021.01); *A61M 60/833* (2021.01); *A61M 60/857* (2021.01); *A61M 2202/0405* (2013.01); *A61M 2205/32* (2013.01); *A61M 2205/33* (2013.01); *A61M 2205/3303* (2013.01)

(58) Field of Classification Search
CPC .......... A61M 2205/32; A61M 2205/33; A61M 1/101; A61M 1/006; A61M 1/1018; A61M 1/1029; A61M 1/125; A61M 2025/1052; A61M 2205/3303; A61M 25/0017; A61M 25/10
See application file for complete search history.

(56) References Cited

U.S. PATENT DOCUMENTS

| | | | |
|---|---|---|---|
| 4,714,460 A | 12/1987 | Calderon | |
| 4,822,341 A | 4/1989 | Colone | |
| 4,838,864 A | 6/1989 | Peterson | |
| 4,957,484 A | 9/1990 | Murtfeldt | |
| 5,005,564 A | 4/1991 | Grundei et al. | |
| 5,069,662 A | 12/1991 | Bodden | |
| 5,097,840 A | 3/1992 | Wallace et al. | |
| 5,366,504 A | 11/1994 | Andersen et al. | |
| 5,391,143 A | 2/1995 | Kensey | |
| 5,484,412 A | 1/1996 | Pierpont | |
| 5,509,897 A | 4/1996 | Twardowski et al. | |
| 5,554,119 A | 9/1996 | Harrison et al. | |
| 5,558,642 A | 9/1996 | Schweich, Jr. et al. | |
| 5,716,340 A | 2/1998 | Schweich, Jr. et al. | |
| 5,817,046 A | 10/1998 | Glickman | |
| 5,836,912 A | 11/1998 | Kusleika | |
| 5,893,841 A | 4/1999 | Glickman | |
| 5,897,533 A | 4/1999 | Glickman | |
| 5,908,407 A | 6/1999 | Frazee et al. | |
| 5,919,163 A | 7/1999 | Glickman | |
| 5,921,913 A | 7/1999 | Siess | |
| 6,042,569 A | 3/2000 | Finch, Jr. et al. | |
| 6,139,517 A | 10/2000 | Macoviak et al. | |
| 6,152,945 A | 11/2000 | Bachinski et al. | |
| 6,165,196 A | 12/2000 | Stack et al. | |
| 6,179,796 B1 | 1/2001 | Waldridge | |
| 6,183,492 B1 | 2/2001 | Hart et al. | |
| 6,248,091 B1 | 6/2001 | Voelker | |
| 6,254,563 B1 | 7/2001 | Macoviak et al. | |
| 6,503,224 B1 | 1/2003 | Forman et al. | |
| 6,524,323 B1 | 2/2003 | Nash et al. | |
| 6,555,057 B1 | 4/2003 | Bendera | |
| 6,616,623 B1 | 9/2003 | Kutushov | |
| 6,635,068 B1 | 10/2003 | Dubrul et al. | |
| 6,699,231 B1 | 3/2004 | Sterman et al. | |
| 6,878,140 B2 | 4/2005 | Barbut | |
| 6,936,057 B1 | 8/2005 | Nobles | |
| 7,022,097 B2 | 4/2006 | Glickman | |
| 7,195,608 B2 | 3/2007 | Burnett | |
| 7,645,259 B2 | 1/2010 | Goldman | |
| 7,766,892 B2 | 8/2010 | Keren et al. | |
| 7,780,628 B1 | 8/2010 | Keren et al. | |
| 8,109,880 B2 | 2/2012 | Pranevicius et al. | |
| 8,126,538 B2 | 2/2012 | Shuros et al. | |
| 8,216,122 B2 | 7/2012 | Kung | |
| 8,480,555 B2 | 7/2013 | Kung | |
| 8,679,057 B2 | 3/2014 | Fulton, III et al. | |
| 9,179,921 B1 | 11/2015 | Morris | |
| 9,405,942 B2 | 8/2016 | Liao et al. | |
| 9,421,316 B2 | 8/2016 | Leeflang et al. | |
| 9,433,713 B2 | 9/2016 | Corbett et al. | |
| 9,486,566 B2 | 11/2016 | Siess | |
| 9,533,054 B2 | 1/2017 | Yan et al. | |
| 9,533,084 B2 | 1/2017 | Siess et al. | |
| 9,642,991 B2 | 5/2017 | Eversull et al. | |
| 9,669,142 B2 | 6/2017 | Spanier et al. | |
| 9,669,144 B2 | 6/2017 | Spanier et al. | |
| 9,675,739 B2 | 6/2017 | Tanner et al. | |
| 9,682,223 B2 | 6/2017 | Callaghan et al. | |
| 9,750,861 B2 | 9/2017 | Hastie et al. | |
| 9,878,080 B2 | 1/2018 | Kaiser et al. | |
| 9,901,722 B2 | 2/2018 | Nitzan et al. | |
| 10,149,684 B2 | 12/2018 | Nitzan et al. | |
| 10,154,846 B2 | 12/2018 | Nitzan et al. | |
| 10,195,405 B2 | 2/2019 | Nitzan et al. | |
| 10,207,086 B2 | 2/2019 | Nitzan et al. | |
| 10,226,604 B2 | 3/2019 | Nitzan et al. | |
| 10,226,605 B2 | 3/2019 | Nitzan et al. | |
| 10,245,363 B1 | 4/2019 | Rowe | |
| 10,285,708 B2 | 5/2019 | Nitzan et al. | |
| 10,300,254 B2 | 5/2019 | Nitzan et al. | |
| 10,639,460 B2 | 5/2020 | Nitzan et al. | |
| 10,653,871 B2 | 5/2020 | Nitzan et al. | |
| 10,709,878 B2 | 7/2020 | Nitzan et al. | |
| 10,912,873 B2 | 2/2021 | Nitzan et al. | |
| 10,926,069 B2 | 2/2021 | Nitzan et al. | |
| 10,960,189 B2 | 3/2021 | Nitzan et al. | |
| 2003/0093109 A1 | 5/2003 | Mauch | |
| 2003/0134416 A1 | 7/2003 | Yamanishi et al. | |
| 2004/0006306 A1 | 1/2004 | Evans et al. | |
| 2004/0064091 A1 | 4/2004 | Keren et al. | |
| 2004/0147871 A1 | 7/2004 | Burnett | |
| 2004/0210296 A1 | 10/2004 | Schmitt et al. | |
| 2004/0230181 A1 | 11/2004 | Cawood | |
| 2005/0228474 A1 | 10/2005 | Laguna | |
| 2005/0251180 A1 | 11/2005 | Burton et al. | |
| 2006/0030814 A1 | 2/2006 | Valencia et al. | |
| 2006/0064059 A1 | 3/2006 | Gelfand et al. | |
| 2006/0100658 A1 | 5/2006 | Obana et al. | |
| 2006/0178604 A1 | 8/2006 | Aiderman | |
| 2007/0055299 A1 | 3/2007 | Ishimaru et al. | |
| 2007/0282303 A1 | 12/2007 | Nash et al. | |
| 2007/0282382 A1 | 12/2007 | Shuros et al. | |
| 2008/0009719 A1 | 1/2008 | Shuros et al. | |
| 2008/0015628 A1 | 1/2008 | Dubrul et al. | |
| 2008/0071135 A1 | 3/2008 | Shaknovich | |
| 2008/0097412 A1 | 4/2008 | Shuros et al. | |
| 2008/0103573 A1 | 5/2008 | Gerber | |
| 2008/0140000 A1 | 6/2008 | Shuros et al. | |
| 2008/0294228 A1 | 11/2008 | Brooke et al. | |
| 2009/0018526 A1 | 1/2009 | Power et al. | |
| 2009/0112184 A1 | 4/2009 | Fierens et al. | |
| 2009/0131785 A1 | 5/2009 | Lee et al. | |
| 2010/0168649 A1 | 7/2010 | Schwartz et al. | |
| 2010/0179389 A1 | 7/2010 | Moroney, III et al. | |
| 2010/0280451 A1 | 11/2010 | Teeslink et al. | |
| 2011/0004046 A1* | 1/2011 | Campbell | A61M 1/101 600/16 |
| 2011/0092955 A1 | 4/2011 | Purdy et al. | |
| 2011/0257462 A1* | 10/2011 | Rodefeld | A61M 60/205 600/16 |

(56) References Cited

U.S. PATENT DOCUMENTS

| | | |
|---|---|---|
| 2011/0276023 A1 | 11/2011 | Leeflang et al. |
| 2011/0282274 A1 | 11/2011 | Fulton, III |
| 2011/0295302 A1 | 12/2011 | Mohl |
| 2012/0029466 A1 | 2/2012 | Callaghan et al. |
| 2012/0157913 A1* | 6/2012 | Aziz ............... A61M 39/24 604/28 |
| 2012/0259215 A1 | 10/2012 | Gerrans et al. |
| 2013/0096476 A1 | 4/2013 | Rogachevsky |
| 2013/0096494 A1 | 4/2013 | Kassab |
| 2013/0138041 A1 | 5/2013 | Smisson, III et al. |
| 2013/0237954 A1 | 9/2013 | Shuros et al. |
| 2013/0245607 A1 | 9/2013 | Eversull et al. |
| 2013/0317535 A1 | 11/2013 | Demmy |
| 2013/0338559 A1 | 12/2013 | Franano et al. |
| 2014/0010686 A1 | 1/2014 | Tanner et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0296615 A1 | 10/2014 | Franano |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0283360 A1* | 10/2015 | Kelly ............... A61M 25/1002 604/509 |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0129266 A1 | 5/2016 | Schmidt |
| 2016/0169630 A1 | 6/2016 | Augustine et al. |
| 2016/0331378 A1 | 11/2016 | Nitzan et al. |
| 2017/0014563 A1 | 1/2017 | Khir |
| 2017/0095395 A1 | 4/2017 | Wennen et al. |
| 2017/0197021 A1 | 7/2017 | Nitzan et al. |
| 2017/0224512 A1 | 8/2017 | Hingston |
| 2018/0125499 A1 | 5/2018 | Nitzan et al. |
| 2018/0126130 A1 | 5/2018 | Nitzan et al. |
| 2018/0146968 A1 | 5/2018 | Nitzan et al. |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1 | 9/2018 | Nitzan et al. |
| 2019/0014991 A1 | 1/2019 | Maki et al. |
| 2019/0083761 A1 | 3/2019 | Nitzan et al. |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0366063 A1 | 12/2019 | Nitzan et al. |
| 2020/0016383 A1 | 1/2020 | Nitzan et al. |
| 2020/0046372 A1 | 2/2020 | Nitzan |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0397963 A1 | 12/2020 | Nitzan et al. |
| 2021/0121678 A1 | 4/2021 | Nitzan et al. |

FOREIGN PATENT DOCUMENTS

| | | |
|---|---|---|
| EP | 2353503 A1 | 8/2011 |
| EP | 2637927 A1 | 9/2013 |
| WO | 89/04193 A1 | 5/1989 |
| WO | 01/013983 A2 | 3/2001 |
| WO | 2012/135834 A2 | 10/2012 |
| WO | 2013/025826 A1 | 2/2013 |
| WO | 2013/061281 A1 | 5/2013 |
| WO | 2014/141284 A2 | 9/2014 |
| WO | 2015/186003 A2 | 12/2015 |
| WO | 2017/087556 A1 | 5/2017 |
| WO | 2018172848 A2 | 9/2018 |

OTHER PUBLICATIONS

International Search Report and Written Opinion dated Jun. 25, 2018, for PCT/IB18/00263, filed Mar. 1, 2018 (10 pages).

International Search Report and Written Opinion dated Oct. 30, 2018, for PCT/IB18/000364, filed Mar. 19, 2018 (9 pages).

Non-Final Office Action issued in U.S. Appl. No. 15/799,562, dated Jul. 28, 2020 (8 pages).

Non-Final Office Action issued in U.S. Appl. No. 15/870,111, dated Jun. 24, 2020 (5 pages).

Non-Final Rejection issued in U.S. Appl. No. 16/867,047, dated Sep. 16, 2020 (11 pages).

Bannon, 2011, Anatomic considerations for central venous cannulation, Risk Manag Healthc Policy 4:27-39.

Moscucci, 2014, Section III Hemodynamic principles 10 Pressure measurement, 223-244 in Grossman & Baim's Cardiac Catheterization, Angiography, and Intervention 8 Ed.

Shimizu, 2014, Embolization of a fractured central venous catheter placed using the internal jugular apporach, Int J Surg Case Rep 5:219.

Stone, 2010, The effect of rigid cervical collars on internal jugular vein dimensions, Acad Emerg Med 17(1): 100-102.

Swan, 1970, Catheterization of the Heart in Man with Use of a Flow-directed Balloon-tipped Catheter, NEJM 283 (9):447-451.

Yancy, 2013, 2013 ACCF/AHA Guideline for the Management of Heart Failure, Circulation 128(16):e240-e327.

\* cited by examiner

SYSTEMS AND METHODS FOR REDUCING PRESSURE AT AN OUTFLOW OF A DUCT

CROSS REFERENCE

The present application is a continuation of U.S. patent application Ser. No. 15/867,003, filed Jan. 10, 2018, which application is a continuation of U.S. patent application Ser. No. 15/150,637, filed May 10, 2016, now issued as U.S. Pat. No. 10,149,684, which application claims priority to U.S. Provisional Patent Application No. 62/159,465, filed May 11, 2015, and to U.S. Provisional Patent Application No. 62/233,802, filed Sep. 28, 2015, which are hereby incorporated by reference in their entireties.

FIELD

The present disclosure relates generally to systems and methods for reducing pressure at an outflow of a duct.

BACKGROUND

The lymphatic system is part of the circulatory system in conjunction with the arterial and venous systems. A primary function of the lymphatic system is to drain excessive interstitial fluid back into the venous system at two main locations: the thoracic duct and the lymphatic duct, which drain into the left and right subclavian veins, respectively.

Under normal circulatory conditions of the arterial and venous systems the interstitial fluid volume balance is maintained and the lymph fluid is cleared back through the lymphatic system. In pathological conditions such as Acute Cardiogenic Pulmonary Edema and chronic heart failure, the capillary hydrostatic pressure and the venous pulmonary pressure can become elevated and fluid flows excessively out of the blood vessels and into the interstitial and alveolar spaces. The pressure gradient between the initial lymphatics and at the outflow of the thoracic duct and the lymphatic duct is reduced and the lymphatic system cannot clear the additional fluid which accumulates in the air spaces of the lungs. This is a life threatening condition as gas exchange is impaired to the extent that it may lead to respiratory failure.

Current treatment methods require extended hospitalization and treatment with loop diuretics and/or vasodilators. Oftentimes patients must also receive supplemental oxygen or, in more extreme cases, require mechanical ventilation. Many of these treatment methods are less than ideal because the edema is not always alleviated rapidly enough and for many patients renal function is adversely affected. A significant percentage of patients do not respond to this treatment and a significant percentage must be readmitted to a hospital within thirty days.

A significant problem with current treatment protocol is that it is based on the need to reduce intravascular blood pressure to move interstitial and lymphatic fluid back into the vasculature. The reduction of intravascular blood pressure may lead to hypotension and may activate the Renin Angiotenesin Aldesterone System, which may lead back to an increase in blood pressure or to worsening of renal function. Eventually, this cycle leads to diuretic resistance and the worsening of renal function in almost 30% of admitted patients. The lymphatic system can directly drain fluids from the interstitial compartment into the intravascular compartment and by such to relief edema.

The lymphatic system drains the interstitial fluids via the thoracic duct and right lymphatic duct that drain into the region around the bifurcation of the left subclavian vein and left internal jugular vein for the thoracic duct and into the bifurcation of the right internal jugular vein and right subclavian vein for the right lymphatic duct. However, in conditions such as acutely decompensated heart failure the lymphatic return is reduced as a result of elevated central venous pressure (CVP). Therefore, as a result of the elevated CVP, the lymphatic return is greatly reduced.

Accordingly, there remains a need for improved systems and methods for reducing pressure at an outflow of a duct such as the thoracic duct or the lymphatic duct.

SUMMARY

Various devices, methods, and systems are provided for treating edema. An indwelling catheter configured to be implantable within a vein of a patient is provided that in one embodiment includes a sheath at least partially implantable within a patient's vein. The sheath has a lumen extending therethrough and a catheter shaft movably positioned within and extending through the lumen of the sheath. The indwelling catheter also includes a catheter shaft movably positioned within and extending through the lumen of the sheath. The catheter shaft is configured to be at least partially implantable within a patient's vein and a proximal end can extend from a proximal end of the sheath and a distal end can extend from a distal end of the sheath. The catheter shaft has a suction lumen extending therethrough, and one or more suction ports disposed therein and in fluid communication with the suction lumen. The indwelling catheter also includes a flexible membrane attached to a distal portion of the catheter shaft. The flexible membrane is a collapsible, tube-like member having a lumen extending therethrough. The indwelling catheter also includes a selectively deployable restriction member formed over a portion of the flexible membrane, and an inflation lumen extending through the catheter shaft. The at least one inflation lumen is in fluid communication with the restriction member.

The indwelling catheter also includes can vary in any number of ways. For example, the indwelling catheter can include a cone shaped tip at the distal end of the catheter shaft. For another example, the flexible membrane can be coupled to an outer wall of the catheter shaft along a length of the flexible membrane. The flexible membrane can be bonded or welded to the catheter shaft along one or several segments and along about 10 to 360 degrees of a circumference of the catheter shaft, e.g., along about 180 to 270 degrees of a circumference of the catheter shaft.

For yet another example, the flexible membrane can be oriented so as to be substantially parallel to the catheter shaft. For still another example, the restriction member can be a selectively expandable balloon coupled to an outer wall of the flexible membrane.

For another example, the indwelling catheter can include a second selectively deployable restriction member formed over a distal portion of the flexible membrane. The restriction member can be formed over a proximal portion of the flexible membrane, and the at least one inflation lumen can be in fluid communication with the second restriction member. The second selectively deployable restriction member can be a selectively expandable balloon coupled to an outer wall of the flexible membrane. The indwelling catheter can include a first pressure port disposed proximally of the restriction member, and a second pressure port disposed between the selectively deployable restriction members. Instead of using pressure ports, a miniature pressure sensor can be mounted on the catheter at the same locations. For yet another example, the indwelling catheter can include a first pressure port disposed distally to the second restriction member, and a second pressure port disposed between the selectively deployable restriction members. Instead of using pressure ports, a miniature pressure sensor can be mounted on the catheter at the same locations. For another example, the indwelling catheter can include a first pressure port disposed proximally of the restriction member, a second pressure port disposed between the selectively deployable restriction members, and a third pressure port disposed distally to the second restriction member. Instead of using pressure ports, a miniature pressure sensor can be mounted on the catheter at the same locations.

For yet another example, the indwelling catheter can include a first inflation port disposed in an outer wall of the flexible membrane and in fluid communication with the first selectively deployable restriction member. The indwelling catheter can further include a second inflation port disposed on the outer wall of the flexible member and in fluid communication with the second selectively deployable restriction member.

In another aspect, a method of treating edema is provided that in one embodiment includes advancing from a sheath implanted within a vein of a patient a catheter shaft having a flexible and collapsible tubular membrane coupled to an outer wall of the catheter shaft at a distal portion thereof, so as to position the catheter shaft within the vein such that a distal end of the catheter shaft is positioned distally of at least one outflow port of a duct of the lymphatic system. The method also includes actuating a first expandable member attached to the membrane to create a first restriction within the vein adjacent to a proximal region of the flexible membrane of the catheter shaft. The first restriction is positioned proximally of the at least one outflow port. The method also includes actuating a second expandable member attached to the membrane to create a second restriction within the vein distal to the first restriction and adjacent to a distal region of the flexible membrane of the catheter shaft. The second restriction is positioned distally of the at least one outflow port. The first and second restriction members create a localized low pressure zone extending therebetween.

The method can have any number of variations. For example, the method can include implanting the sheath of the catheter system within the vein of the patient.

For another example, the method can include withdrawing fluid from within the low pressure zone through the catheter to a pump and returning fluid to a vein such that the returned fluid passes through the membrane to bypass the low pressure zone. Withdrawing fluid can be accomplished by passing fluid from within the low pressure zone through a suction port disposed in a wall of the catheter shaft and in fluid communication with the low pressure zone between the first and second restrictions. The suction port can be in communication with a suction tubing line of the catheter to withdraw fluid from the vein through an action of the pump and return fluid to venous circulation through the suction tubing line coupled to a proximal end of the catheter sheath wherein the fluid is discharged at a distal end of the catheter sheath proximal to the first restriction. The catheter can be implanted in one of the right and left internal jugular veins and advanced to a position such that the second restriction is distal to a junction of a subclavian vein and an internal jugular vein, the first restriction can be within the internal jugular vein, and the second restriction can be within an innominate vein and the suction port is adjacent to the junction of the subclavian vein. The catheter can be implanted in one of the right and left internal jugular veins and advanced to a position such that the second restriction is distal to a junction of a subclavian vein and an internal jugular vein, and the first restriction can be within the internal jugular vein, the second restriction can be within an innominate vein, and the suction port can be adjacent to the junction of the subclavian vein. The catheter can be implanted in one of the right and left internal jugular veins and advanced to a position such that the second restriction is distal to a junction of both innominate veins, and the first restriction can be within the internal jugular vein, the second restriction can be within a superior vena cava (SVC) vein (also referred to as an innominate vein), and the suction port can be adjacent to a junction of the subclavian vein.

For yet another example, transporting the fluid through the localized low pressure zone via the flexible membrane can maintain a constant pressure within the low pressure zone.

In another aspect, a system for treating edema is provided that in one embodiment includes an indwelling catheter system configured for at least partial placement within a vein of a patient. The indwelling catheter system has an implantable sheath with a lumen extending therethrough, and a catheter shaft movably positioned within and extending through the lumen of the sheath. The catheter shaft has one or more suction ports disposed therein. The indwelling catheter system also has a flexible membrane attached to a distal portion of the catheter shaft, a first selectively deployable restriction member formed over a proximal portion of the flexible membrane, and a second selectively deployable restriction member formed over a distal portion of the flexible membrane and an inflation lumen extending through the catheter shaft. The inflation lumen is in fluid communication with the first and the second restriction members. The system for treating edema further includes a pump configured to create a pressure differential to withdraw fluid from the suction port and through a suction lumen from the catheter shaft to withdraw a fluid within the vein from venous circulation and to return the fluid to venous circulation through the catheter system, a plurality of pressure sensors disposed within the catheter system, and a control module configured to control operation of the system.

The system for treating edema can have any number of variations. For example, the system for treating edema can include a pump configured to be external to the patient. For another example, the pump can be a peristaltic flow pump.

Various systems and methods are provided for reducing pressure at an outflow of a duct such as the thoracic duct or the lymphatic duct. A medical system is provided that in one embodiment includes a catheter shaft configured to be positioned within a vein of a patient, a first selectively deployable restrictor coupled to the catheter shaft and configured to be positioned within the vein, a second selectively deployable restrictor coupled to the catheter shaft at a location distal to the first restrictor such that a distance spans between the first and second restrictors, at least one inlet opening formed through a sidewall of the catheter shaft at a location between the first and second restrictors, and a pump configured to facilitate suction of fluid into the catheter shaft through the at least one inlet opening. The second restrictor is configured to be positioned within the vein.

The medical system can have any number of variations. For example, the first and second restrictors can each include a balloon. The medical system can include at least one inflation lumen extending along the catheter shaft. The at least one inflation lumen can be in fluid communication with the first and second restrictors. The at least one inflation lumen can include a single lumen in fluid communication with both of the first and second restrictors, or the at least one inflation lumen can include a first inflation lumen in fluid communication with the first restrictor and a second inflation lumen in fluid communication with the second restrictor.

For another example, the first restrictor can be movable between an activated configuration in which the first restrictor has a first diameter and a relaxed configuration in which the first restrictor has a second diameter that is less than the first diameter, and the second restrictor can be movable between an activated configuration in which the second restrictor has a third diameter and a relaxed configuration in which the second restrictor has a fourth diameter that is less than the third diameter. The first diameter can be equal to the third diameter, or the first diameter can be less than the third diameter.

For yet another example, the first and second restrictors can each include a stent. For still another example, the medical system can include at least one additional inlet opening formed through the sidewall of the catheter shaft at a location that is proximal to the first and second restrictors. For another example, the catheter shaft can have an open distal end. For yet another example, the pump can include an impeller within the catheter shaft. For another example, the pump can be configured to be positioned within the vein, or the pump can be non-implantable. For still another example, the medical system can include at least one sensor.

For another example, the medical system can include a controller configured to actuate the pump. The controller can be configured to actuate the pump in response to user operation of a control external to the body of the patient. The medical system can include a pressure sensor configured to be implanted in the body of the patient, and the controller can be configured to actuate the pump in response to a pressure measured by the pressure sensor exceeding a predefined threshold and/or the controller can be configured to control a speed of operation of the pump depending on a pressure measured by the pressure sensor.

For yet another example, the medical system can include a flexible membrane attached to a distal portion of the catheter shaft. The flexible membrane can be a collapsible, tube-like member having a lumen extending therethrough. The first and second restrictor can each be formed over a portion of the flexible membrane.

For another example, the vein can include an internal jugular vein or a subclavian vein.

In another aspect, a medical method is provided that can include implanting the catheter shaft at least at least partially within a vein of a patient such that the first restrictor is positioned upstream of an outflow port of a duct of the patient's lymphatic system and such that the second restrictor is positioned downstream of the outflow port of the duct.

The medical method can vary in any number of ways. For example, the medical method can include activating the first restrictor of the medical system such that the first restrictor occludes the vein at a first occlusion site, and activating the second restrictor such that the second restrictor occludes the vein at a second occlusion site. Activating the first restrictor can include inflating the first restrictor, and activating the second restrictor can include inflating the second restrictor, and/or activating the first restrictor can include radially expanding the first restrictor, and activating the second restrictor can include radially expanding the second restrictor. For another example, the medical method can include actuating the pump, thereby creating a low pressure zone between the first and second restrictors. For yet another example, the duct can include a thoracic duct. For still another example, the duct can include a lymphatic duct. For another example, the vein can include an internal jugular vein or a subclavian vein.

In another embodiment, a medical system is provided that includes a catheter shaft configured to be positioned within a vein of a patient, and at least one restrictor coupled to the catheter shaft and configured to be positioned within the vein. The at least one restrictor is movable between an activated configuration in which the at least one restrictor has a first diameter and a relaxed configuration in which the at least one restrictor has a second diameter that is less than the first diameter. The at least one restrictor is configured to occlude fluid flow through the vein when the at least one restrictor is in the activated configuration within the vein. The medical system also includes a pump configured to pump fluid through the catheter shaft regardless of whether the at least one restrictor is in the activated configuration or the relaxed configuration.

The medical system can have any number of variations. For example, the at least one restrictor includes a single restrictor. For another example, the at least one restrictor can include first and second restrictors. The second restrictor can be coupled to the catheter shaft at a location distal to the first restrictor such that a distance spans between the first and second restrictors.

For yet another example, the at least one restrictor can include a balloon. The medical system can include at least one inflation lumen extending along the catheter shaft. The at least one inflation lumen can be in fluid communication with the at least one restrictor.

For still another example, the at least one restrictor can include a stent. For yet another example, the pump can include an impeller within the catheter shaft. For another example, the pump can be configured to be positioned within the vein, or the pump can be non-implantable. For still another example, the medical system can include at least one sensor.

For yet another example, the medical system can include a controller configured to actuate the pump. The controller can be configured to actuate the pump in response to user operation of a control external to the body of the patient. The medical system can include a pressure sensor configured to be implanted in the body of the patient, and the controller can be configured to actuate the pump in response to a pressure measured by the pressure sensor exceeding a predefined threshold and/or can be configured to control a speed of operation of the pump depending on a pressure measured by the pressure sensor.

For still another example, the medical system can include a flexible membrane attached to a distal portion of the catheter shaft. The flexible membrane can be a collapsible, tube-like member having a lumen extending therethrough. The at least one restrictor can be formed over a portion of the flexible membrane.

For another example, the vein can include an internal jugular vein or a subclavian vein.

In another aspect, a medical method is provided that includes implanting the catheter shaft of the medical system at least at least partially within a vein of a patient such that the at least one restrictor is positioned upstream of an outflow port of a duct of the patient's lymphatic system.

The medical method can have any number of variations. For example, the medical method can include activating the at least one restrictor such that the at least one restrictor occludes the vein. Activating the at least one restrictor can include inflating the at least one restrictor and/or radially expanding the at least one restrictor.

For another example, the medical method can include actuating the pump, thereby creating a low pressure zone adjacent the duct. For yet another example, the duct can include a thoracic duct. For still another example, the duct can include a lymphatic duct. For another example, the vein can include an internal jugular vein or a subclavian vein.

In another embodiment, a medical method is provided that includes at least partially implanting a catheter shaft within a vein of a patient, thereby positioning a first restrictor coupled to the catheter shaft at a location that is upstream of an outflow port of a duct of the patient's lymphatic system and positioning a second restrictor coupled to the catheter shaft at a location that is downstream of the outflow port of the duct. The catheter shaft has a pump coupled thereto. The medical method also includes, after the first restrictor is positioned, actuating the first restrictor to move the first restrictor from a relaxed configuration to an activated configuration. The medical method also includes, after the second restrictor is positioned, actuating the second restrictor to move the second restrictor from a relaxed configuration to an activated configuration. The medical method also includes, after the first and second restrictors are actuated, actuating the pump to cause a low pressure zone to be created along the catheter between the first and second restrictors.

The medical method can vary in any number of ways. For example, actuating the first restrictor can include inflating the first restrictor, and actuating the second restrictor can include inflating the second restrictor. For another example, actuating the first restrictor can include radially expanding the first restrictor, and actuating the second restrictor can include radially expanding the second restrictor. For yet another example, the medical method can include, after the pump is actuated, re-actuating the first restrictor to move the first restrictor from the activated configuration to the relaxed configuration, and re-actuating the second restrictor to move the second restrictor from the activated configuration to the relaxed configuration. After re-actuating the first and second restrictors, the catheter shaft and the first and second restrictors can be removed from the patient.

For still another example, the pump can be actuated in response to user operation of a control external to the body of the patient. For another example, the pump can be actuated periodically or continuously. For yet another example, the duct can include a thoracic duct of the patient. For still another example, the duct can include a lymphatic duct of the patient. For another example, the vein can include an internal jugular vein of the patient or a subclavian vein of the patient.

For yet another example, the medical method can include implanting a pressure sensor in a location within the body of the patient that enables the pressure sensor to measure pressure in a desired region of the body of the patient. The medical method can include measuring the pressure in the desired region using the pressure sensor, and actuating the pump in response to the measured pressure exceeding a predefined threshold and/or controlling a speed of operation of the pump depending on the measured pressure.

BRIEF DESCRIPTION OF DRAWINGS

This invention will be more fully understood from the following detailed description taken in conjunction with the accompanying drawings, in which.

DETAILED DESCRIPTION

Figure 1:
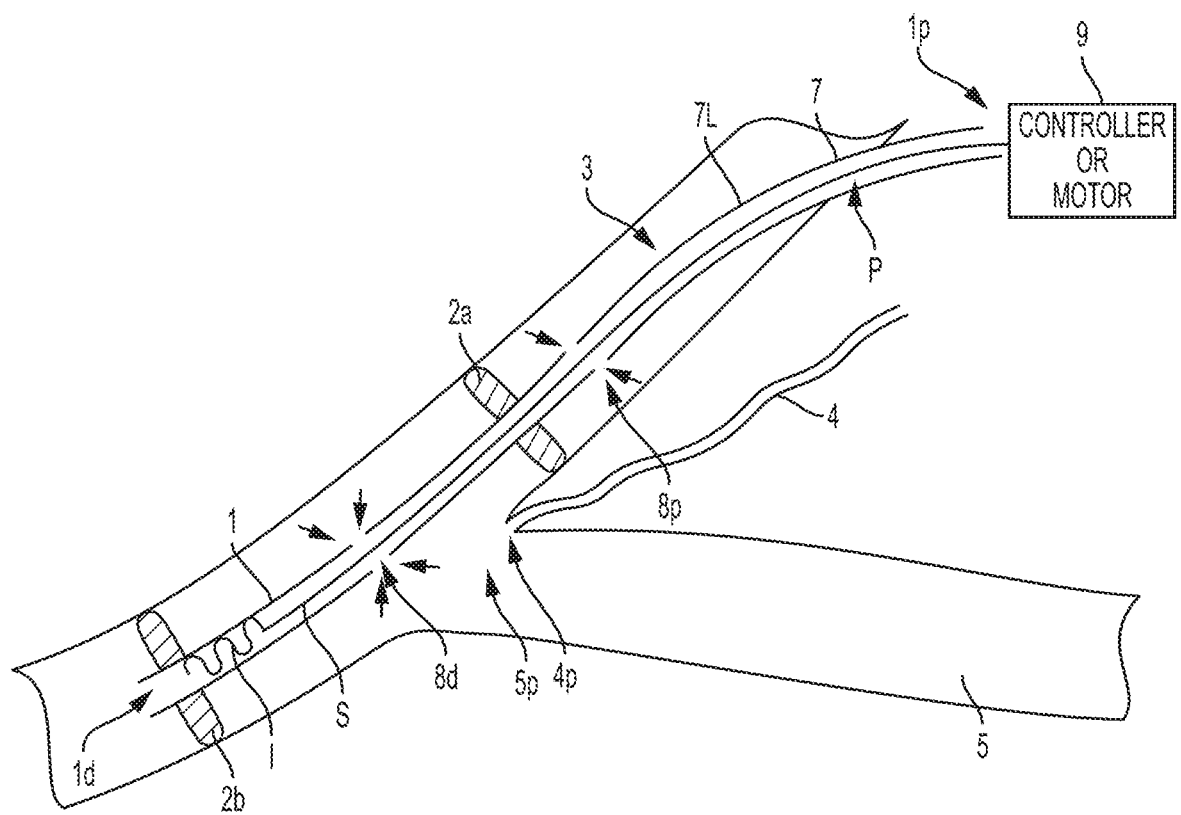
FIG. 1 is a schematic cross-sectional view of one embodiment of a catheter implanted in a vein of a patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments." "some embodiments," "one embodiment," or "an embodiment," or the like, means that a particular feature, structure, or characteristic described in connection with the embodiment is included in at least one embodiment. Thus, appearances of the phrases "in various embodiments." "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal." "up," and "down" may be used herein with respect to the illustrated embodiments. However, surgical instruments may be used in many orientations and positions, and these terms are not intended to be limiting and absolute.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various systems and methods are provided for reducing pressure at an outflow of a duct such as the thoracic duct or the lymphatic duct. In general, the systems and methods may be effective to reduce edema conditions, such as pulmonary edema, in a patient by lowering an outflow pressure in a region around the patient's thoracic/lymphatic duct outflow. As a result of lowering the outflow pressure at the thoracic and/or lymphatic ducts, higher lymphatic return will be achieved, enabling the lymphatic vessel flow to be at or near normal levels. The systems and methods may be effective to rapidly alleviate conditions of the edema and increase the patient response rate. In an exemplary embodiment, the systems and methods may be particularly useful to treat acute pulmonary edema, however a person skilled in the art will appreciate that the systems and methods can be used in various procedures for treating a lymphatic system fluid clearance imbalance.

In one embodiment, an indwelling catheter can be configured to be at least partially implanted (e.g., partially implanted or fully implanted) within a vein of a patient in the vicinity of an outflow port of a duct of the lymphatic system, e.g., in the vicinity of an outflow port of the thoracic duct or in the vicinity of an outflow port of the lymphatic duct. Exemplary materials from which the catheter can be made include polyurethanes. The catheter can include first and second restrictors (also referred to herein as "restriction members") each configured to at least partially occlude the vein within which the catheter is implanted and thus to restrict fluid flow within the vein when the restrictors are activated. The restrictors can each be configured to move between an activated configuration, in which the restrictor occludes the vein, and a relaxed configuration, in which the restrictor does not occlude the vein. The restrictors can each be in the relaxed configuration during implantation of the catheter to ease introduction of the catheter into the patient's body and into the vein. Each of the restrictors can include a balloon configured to be inflated where in the relaxed configuration the balloon is not inflated and in the activated configuration in which the balloon is inflated. The restrictors can be made from any one or more of a variety of materials configured to expand upon the delivery of a fluid thereto and to contract upon the withdrawal of the fluid. Exemplary materials from which the balloon can be made include polymeric materials such as PEBAX, silicones, polyurethanes, and nylons. The catheter can include at least one inflation lumen through which an inflation fluid (e.g., air, liquid, etc.) can be introduced to inflate/deflate the restrictors. The at least one inflation lumen can include one lumen in fluid communication with both of the restrictors such that the restrictors can be simultaneously inflated/deflated, or can include first and second lumens with the first lumen in fluid communication with the first restrictor and the second lumen in fluid communication with the second restrictor such that the restrictors can be selectively inflated simultaneously or sequentially. The catheter can include a pump, such as an axial motor pump, configured to pump fluid through the catheter. The catheter can be coupled to a motor configured to drive the pump. The motor can be included in the catheter (e.g., within a shaft of the catheter) and be configured to be implanted with the catheter, or the motor can be located outside of the catheter (e.g., outside of the catheter's shaft) and be configured to be located outside of the patient rather than be implanted therein.

In one embodiment of using the catheter, the catheter can be positioned at a desired location within the vein. The first and second restrictors can then each be activated (simultaneously or sequentially) to move from the relaxed configuration to the activated configuration. The first and the second restrictors, when activated so as to provide two occlusions within the vein, define a low pressure zone therebetween within a portion of the vein in which the catheter is positioned. Higher pressure zones accordingly exist on either side of the restrictors. The motor can drive the pump to induce the low pressure zone by causing fluid to be pumped through the catheter. The catheter and the restrictors can be positioned within the vein such that the low pressure zone is adjacent to an outflow port of a duct (e.g., the thoracic duct or the lymphatic duct) to allow fluid to pass from the lymph duct outflow port to the portion of the catheter housed within the vein so that fluid can flow out of the catheter.

In at least some embodiments, the restrictor(s) of a catheter can be inflated and deflated from time to time to enable free flow of blood in a patient's vein in which the restrictor(s) are positioned and thus enable the system to stop working for a period of time. This period of time can be required in such treatments to allow for the assessment of the patient's clinical condition, allow the patient to undergo other treatments or enable him to go to the bathroom and/or to wash any stagnation points that might have occurred.

The catheters described herein can be configured to be placed in a patient's body for up to about seventy-two hours, e.g., the catheter can be indwelled in the body for up to about seventy-two hours. The catheter systems described herein that include the catheters can be operated in a treatment time period in a range of about 6 to 8 hours. At the end of each treatment period, the restrictors are deflated, the catheter can be filled with a heparin catheter locking solution, and an assessment of the patient's clinical condition can be performed. The catheter system can be operated again if desired by medical personnel. Within the indwelling period of the catheter, a number of treatment periods can be in a range of 3 to 6 cycles, e.g., for a maximum of about forty hours of operation within a seventy-two hour indwelling period.

A person skilled in the art will appreciate that the systems and methods disclosed herein can be used with a variety of surgical devices, including measuring devices, sensing devices, locator devices, insertion devices, etc.

FIG. 1 illustrates one embodiment of a catheter 1 that includes at least one restrictor 2a, 2b. The at least one restrictor includes first and second restrictors 2a, 2b in this illustrated embodiment, which each include a balloon configured to be inflated (corresponding to an activated configuration) and deflated (corresponding to a relaxed configuration). The first and second restrictors 2a, 2b can be spaced a distance apart from one another along a longitudinal length of the catheter 1 such that one of the restrictors 2b is more distal than the other of the restrictors 2a. The distance between the first and second restrictors 2a, 2b can define a length of a low pressure zone that can be created when the catheter 1 is implanted within a vein. FIG. 1 shows the catheter 1 positioned within an internal jugular vein 3 of a patient with the distal restrictor 2b positioned distal to an outflow port 4p of the patient's thoracic duct 4 and the proximal restrictor 2a positioned proximal to the outflow port 4p of the patient's thoracic duct 4. The low pressure zone defined between the proximal and distal (first and second) restrictors 2a, 2b can thus be located adjacent the outflow port 4p of the thoracic duct 4. The proximal restrictor 2a being positioned proximal to (e.g., upstream) of the outflow port 4p of the thoracic duct 4 may help prevent back flow from the patient's subclavian vein 5 while providing the low pressure zone and benefit(s) thereof. The catheter 1 can be similarly positioned on a right side of the patient with the distal restrictor 2b positioned distal to an outflow port of the patient's subclavian vein 5 and an outflow port of the patient's lymphatic duct (not shown) and the proximal restrictor 2a positioned proximal to the outflow port of the patient's subclavian vein 5 and the outflow port of the patient's lymphatic duct.

The catheter 1 can include at least one inflation lumen (omitted from FIG. 1 for clarity of illustration) configured to facilitate inflation of the first and second restrictors 2a, 2b, e.g., to facilitate movement of the restrictors 2a, 2b between the activated and relaxed configurations. The first and second restrictors 2a, 2b are shown in the activated configuration in FIG. 1 with the first and second restrictors 2a, 2b each abutting an internal surface of the jugular vein 3 so as to provide two, spaced-apart occlusions therein.

The catheter 1 can include a shaft 7 having a lumen 7L, as shown in this illustrated embodiment, configured to communicate fluid therethrough so as to accommodate the flow of fluid in a vein in which the catheter 1 is implanted. The shaft 7 can have a variety of sizes, such as having a diameter that is in the range of about 8 to 18 Fr (e.g., about 8 Fr, equal to or less than about 12 Fr, etc.) and having a length in the range of about 25 to 40 cm.

The first and second restrictors 2a. 2b can be attached to and surround the shaft 7. The first and second restrictors 2a. 2b can each be formed in the shape of a torus, as in this illustrated embodiment, to facilitate the surrounding of the shaft 1 and/or to help prevent compression of the restrictors 2a, 2b when they are moved radially outward during expansion thereof and thereby thus overcoming a possible tendency for the restrictors 2a. 2b to collapse in response to an external pressure. The first and second restrictors 2a, 2b can, however, have other shapes.

The catheter 1 can have a first or distal suction inlet 8d formed through the shaft's sidewall. The distal suction inlet can be in communication with the lumen 7L so as to allow fluid to enter the lumen 7L therethrough, as shown in FIG. 1 by four arrows at the distal suction inlet 8d pointing inward toward the lumen 7L. The distal suction inlet 8d can include any number of openings formed through the shaft's sidewall. The openings can have any of a variety of configurations, e.g., slits, circular holes, ovular holes, rectangular slots, etc. The distal suction inlet 8*d* can be located along the catheter's longitudinal length at a position between the first and second restrictors 2*a*, 2*b*. The distal suction inlet 8*d* can thus be located within the low pressure zone. In an exemplary embodiment, as shown in FIG. 1, in use, the distal suction inlet 8*d* can be positioned adjacent the outflow ports 4*p*. 5*p* of the thoracic duct 4 and the subclavian vein 5 so as to allow fluid exiting the outflow ports 4*p*. 5*p* to enter the catheter 1.

The catheter 1 can include a second or proximal suction inlet 8*p* formed through the shaft's sidewall. The proximal suction inlet 8*p* can be in communication with the lumen 7L so as to allow fluid to enter the catheter's lumen 7L therethrough, as shown in FIG. 1 by two arrows at the proximal suction inlet 8*p* pointing inward toward the lumen 7L. The proximal suction inlet 8*p* can include any number of openings formed through the shaft's sidewall. The openings can have any of a variety of configurations. e.g., slits, circular holes, ovular holes, rectangular slots, etc. The proximal suction inlet 8*p* can be located proximal to the distal suction inlet 8*d* and proximal to the first and second restrictors 2*a*, 2*b*. In an exemplary embodiment, as shown in FIG. 1, in use, the proximal suction inlet 8*p* can be positioned proximal to the outflow ports 4*p*, 5*p* of the thoracic duct 4 and the subclavian vein 5. e.g., upstream thereof. The proximal suction inlet 8*p* may thus allow for regular fluid flow through the jugular vein 3 even when the proximal restrictor 2*a* is activated and occluding the jugular vein 3.

The catheter 1 can include a distal end 1*d* configured to be implanted within the patient's body (e.g., within the jugular vein 3, as shown in this illustrated embodiment) and a proximal end 1*p* configured to not be implanted and instead be located outside the patient's body when the catheter's distal end 1*d* is implanted. The distal end 1*d* of the catheter 1 can be open so as to define a discharge opening of the catheter 1 that allows fluid in the lumen 7L to exit the catheter 1 therethrough. The distal restrictor 2*b* being positioned proximal to the discharge opening may help prevent back flow of fluid exiting the catheter 1 through the discharge opening. The distal restrictor 2*b* can thus be positioned just proximal to the discharge opening to help maximize backflow prevention. The catheter's proximal end 1*p* is configured to not be implanted and is shown outside of the patient's body in FIG. 1. FIG. 1 also shows a controller or motor 9 coupled to the catheter 1 and located outside of and proximal to the catheter's proximal end 1*p* so as to not be within the catheter's shaft 7 and to be located outside of the patient's body. Alternatively, as mentioned above, the catheter's proximal end 1*p* can be configured to be implanted, such as when the controller or motor 9 is included in the catheter's shaft 7.

The catheter 1 can include a pump configured to drive fluid flow through the catheter 1, e.g., through the lumen 7L thereof. The pump can have a variety of configurations. As in this illustrated embodiment, the pump can include an axial motor pump. The axial motor pump can generally be configured like an Archimedes' screw that drives fluid. The axial motor pump can include an impeller I and a drive shaft S (e.g., a cable or a rod) each located in the catheter's shaft 7, e.g., in the lumen 7L. Also as in this illustrated embodiment, the impeller I can be located fully distal to the proximal restrictor 2*a* and can be located at least partially proximal to the second restrictor 2*b* so as to be at least partially located within the low pressure zone and hence near the distal inlet opening. In this illustrated embodiment, the impeller I is fully located within the low pressure zone. The drive shaft S can extend longitudinally through the catheter 1, e.g., through the lumen 7L, to the controller or motor 9. The motor 9 can be configured to drive the drive shaft S, e.g., to rotate the drive shaft S, and hence drive the impeller I, e.g., rotate the impeller I. The drive shaft S can be a solid member, which may provide structural stability to the drive shaft S. Alternatively, the drive shaft S can be hollow, e.g., be cannulated. The drive shaft S being hollow can allow a guide wire to be advanced therethrough, which may facilitate delivery of the catheter 1 into a vein, as will be appreciated by a person skilled in the art, such as by allowing the guide wire to be introduced into a vein and the catheter 20 to then be advanced over the guide wire (and into a sheath (not shown) of the system 10 advanced over the guide wire prior to the catheter 20 being advanced over the guide wire, if the system 10 includes a sheath). For example, the guide wire can be introduced into the jugular vein 3 (e.g., a Seldinger technique via a central venous access under ultrasound guidance), and then the drive shaft S (and the catheter 1 coupled thereto) can be advanced over the guide wire into the jugular vein 3.

The pump can be configured to pump fluid at a variety of rates. In an exemplary embodiment, the pump can be configured to pump fluid at a rate in a range of about 100 to 1000 ml/hour, which can provide a pressure reduction in the low pressure zone from a pressure in a range of about 10 to 20 mmHg (the pressure in the higher pressure zones) to a pressure in a range of about 0 to 6 mmHg (e.g., in a range of about 2 to 4 mmHg, which is a typical normal level, or in a range of about 2 to 5 mmHg, which is also a typical normal level). In at least some embodiments, the pump can have a static, e.g., unchangeable, flow rate. The flow rate can thus be predictable and/or chosen for a specific patient. In other embodiments, the pump can have an adjustable flow rate. The flow rate being adjustable can help the pump accommodate changes in the patient's condition over time and/or allow the pump to be driven at a selected rate for a particular patient. The flow rate can be adjustable in a variety of ways, as will be appreciated by a person skilled in the art, such as by being wirelessly adjusted using a user-operated control device located external to the patient and configured to wirelessly communicate with the pump (e.g., with the controller 9) to adjust the flow rate thereof.

In at least some embodiments, the controller 9 can be configured to be in electronic communication with at least one pressure sensor (not shown). A person skilled in the art will appreciate that a variety of suitable sensors can be used for monitoring pressure, such as central venous pressure (CVP) or other fluid pressure sensors, and blood pressure sensors. The at least one pressure sensor can be implanted in the patient as part of the pump, implanted in the patient as a separate component from the pump, or the at least one pressure sensor can be located external to the patient, such as by being on a skin surface thereof. If not already a part of the pump so as to be in electronic communication therewith, the at least one pressure sensor can be configured to be in electronic communication with the pump over a communication line such as a wired line or a wireless line. In an exemplary embodiment, two pressure sensors can be implanted in the patient. One of the pressure sensors can be implanted between the first and second restrictors 2*a*, 2*b* so as to be in the low pressure zone, and the other one of the pressure sensors can be implanted in the vein either proximal to the proximal restrictor 2*a* (e.g., proximal to the proximal inlet) or distal to the distal restrictor 2*b* (e.g., distal to the discharge opening) so as to be in one of the higher pressure zones. The two sensors can thus allow a pressure differential to be determined between the low pressure zone and the higher pressure zone. In other embodiments, another number of pressure sensors can be implanted in the patient (e.g., one, three, four etc.) and/or the pressure sensor(s) can be implanted at other locations.

The catheter 1 can include at least one lumen (not shown) configured to facilitate use of the pressure sensor(s), for example to facilitate placement of the pressure sensor(s) and/or to be filled with a fluid such as saline to allow for external pressure measurement.

In addition to or instead of the one or more pressure sensors, the controller 9 can be configured to be in electronic communication with at least one other type of sensor (not shown) configured to sense a parameter other than pressure. Examples of sensors that can be used to measure a parameter other than pressure include radio frequency transmitters and receivers, fluid sensors, bioimpedance sensors, heart rate sensors, breathing sensors, activity sensors, and optical sensors. Examples of the measured parameter include fluid amount (e.g., as measured by a fluid sensor, such as a fluid sensor placed in a lung to sense fluid amount in the lung), bioimpedance (e.g., as measured by a bioimpedance sensor), heart rate (e.g., as measured by a heart rate sensor), breathing rate (e.g., as measured by a breathing sensor), patient activity level (e.g., as measured by an activity sensor), and organ dimension (e.g., as measured by an optical sensor). The sensor can be implanted in the patient as part of the pump, implanted in the patient as a separate component from the pump (e.g., implanted in an interstitial space around a lung, implanted at a junction of a right subclavian vein of a patient and an internal jugular vein of the patient, implanted at a junction of a left subclavian vein of a patient and an internal jugular vein of the patient, etc.), or the sensor can be located external to the patient, such as by being on a skin surface thereof. If not already a part of the pump so as to be in electronic communication therewith, the non-pressure sensor(s) can be configured to be in electronic communication with the pump over a communication line such as a wired line or a wireless line. The non-pressure sensor(s) can include one or more sensors. In embodiments including a plurality of sensors, each of the sensors can be configured to measure the same parameter as or a different parameter than any one or more of the other sensors.

The motor 9 can be included as part of the pump and can be configured to be implanted in the patient with the pump, or, as in this illustrated embodiment, the motor 9 can be configured to be non-implantable. The motor 9 being non-implantable can help the pump have a smaller size and/or can allow the pump to be driven by a more powerful motor since the motor 9 can be larger than an implantable motor.

The controller 9 can be included as part of the pump and can be configured to be implanted in the patient with the pump, or, as in this illustrated embodiment, the controller 9 can be configured to be non-implantable. The controller 9 being part of the pump can help allow the pump to be a self-contained system, although in such a controller requires space in the pump, which can increase a size of the pump. The controller 9 being non-implantable can help the pump have a smaller size and/or can allow the pump to be controlled by a more powerful processor since the processor can be more easily upgraded than if implanted with the pump and/or since the processor's size can be less important when outside the pump as opposed to inside the pump.

The controller 9 can include any type of microprocessor or central processing unit (CPU), including programmable general-purpose or special-purpose microprocessors and/or any one of a variety of proprietary or commercially available single or multi-processor systems. The controller 9 can be a component of a control system that includes any number of additional components, such as a memory configured to can provide temporary storage and/or non-volatile storage; a bus system; a network interface configured to enable the control system to communicate with other devices, e.g., other control systems, over a network; and an input/output (I/O) interface configured to connect the control system with other electronic equipment such as I/O devices (e.g., a keyboard, a mouse, a touchscreen, a monitor, etc.) configured to receive an input from a user.

The controller 9 can be configured to receive user input thereto to control any of a variety of aspects related to the catheter 1, such as speed of the motor 9 and ideal range of pressure for the low pressure zone.

In at least some embodiments, the pump can be configured to change its pumping rate (e.g., from zero to a non-zero value, from a non-zero value to zero, or from one non-zero value to another non-zero value) based on pressure measured by the at least one pressure sensor. The controller 9 can be configured to effect such change in response to the sensed pressure. If the measured pressure exceeds a predetermined threshold maximum pressure value, the pump can be configured to increase its pump rate (e.g., increase from zero or increase from some non-zero value) in an effort to decrease the pressure. For example, if the measured pressure within the low pressure zone is too high (e.g., is above a predetermined threshold), the pump can increase its pump rate to decrease the pressure within the low pressure zone. For another example, if the measured pressure within the low pressure zone is below a predetermined threshold, the pump can decrease its pump rate to maintain or increase the pressure within the low pressure zone. For yet another example, if a measured pressure differential between the low pressure zone and the higher pressure zone is not sufficiently great (e.g., is below a predetermined threshold), the pump can increase its pump rate to increase the pressure differential.

In at least some embodiments, the catheter 1 can include only one restrictor, the proximal restrictor 2a. A higher pressure zone can thus be proximal to the proximal restrictor, and a low pressure zone can be distal to the proximal restrictor. The proximal restrictor 2a positioned proximal to (e.g., upstream) of the outflow port 4p of the thoracic duct 4 being the only restrictor of the catheter 1, instead of the distal restrictor 2b positioned distal to (e.g., downstream) of the outflow port 4p of the thoracic duct 4, may help prevent back flow from the subclavian vein 5 while providing the low pressure zone and benefit(s) thereof.

In at least some embodiments, the catheter 1 can have a soft atraumatic tip at its distal end 1d that is tapered in a distal direction and that is flexible. The soft atraumatic tip may facilitate smooth, safe introduction of the catheter 1 into the vein 3. Exemplary materials from which the atraumatic tip can be made include polyurethanes. The catheter may additionally include a flexible extension similar to a guide wire tip and/or have a hydrophilic coating, each of which may further facilitate smooth, safe introduction of the catheter 1 into the vein 3.

In at least some embodiments, the proximal restrictor 2a can be configured to only partially occlude the vein 3 in which the catheter 1 is positioned when the proximal restrictor 2a in its activated configuration. This partial occlusion may facilitate normal fluid flow through the vein 3 even when the proximal restrictor 2a is in the activated configuration. In embodiments in which the proximal restrictor 2a is configured to only partially occlude the vein 3 when in its activated configuration, the catheter 1 can, but need not, include the proximal inlet 8p to facilitate fluid flow through the vein 3. The partial occlusion can be achieved in a variety of ways. For example, the proximal restrictor 2a can have at least one lumen or hole formed therethrough configured to allow fluid flow therethrough when the proximal restrictor 2a is in the activated configuration. For another example, a maximum diameter of the proximal restrictor 2a in the activated configuration can be less than a maximum internal diameter of the vein 3 in which the catheter 1 is positioned to allow fluid flow around an exterior of the proximal restrictor 2a.

In at least some embodiments, the catheter 1 can include at least one lumen or tube (not shown) configured to pass blood therethrough outside the patient's body and back into the patient. Such functionality may allow for the monitoring of blood volume and performing hemofiltration.

In at least some embodiments, the catheter 1 can include one or more radiopaque markers (not shown) configured to be visible using an imaging technique such as fluoroscopy. The one or more radiopaque markers can be on the catheter's shaft 7 at or near one or more features along the shaft 7, such as any or all of the inlet openings or any or all of the restrictors 2a, 2b. The one or more radiopaque markers may thus facilitate proper positioning of the shaft 7 and/or features thereon within a vein. For example, prior to activation of the catheter's restrictor(s) 2a, 2b, the position of the restrictor(s) 2a, 2b within the vein 3 can be verified by visualizing the one or more radiopaque markers using an imaging system.

The first and second restrictors 2a, 2b are discussed with respect to FIG. 1 above as being balloons configured to inflate and deflate, but the first and second restrictors 2a, 2b can have other configurations. For example, the first and second restrictors 2a, 2b can each include a stent configured to expand (corresponding to an activated configuration) and constrict (corresponding to a relaxed configuration). The expandable/constrictable stents can have a variety of configurations, as will be appreciated by a person skilled in the art.

Figure 2:
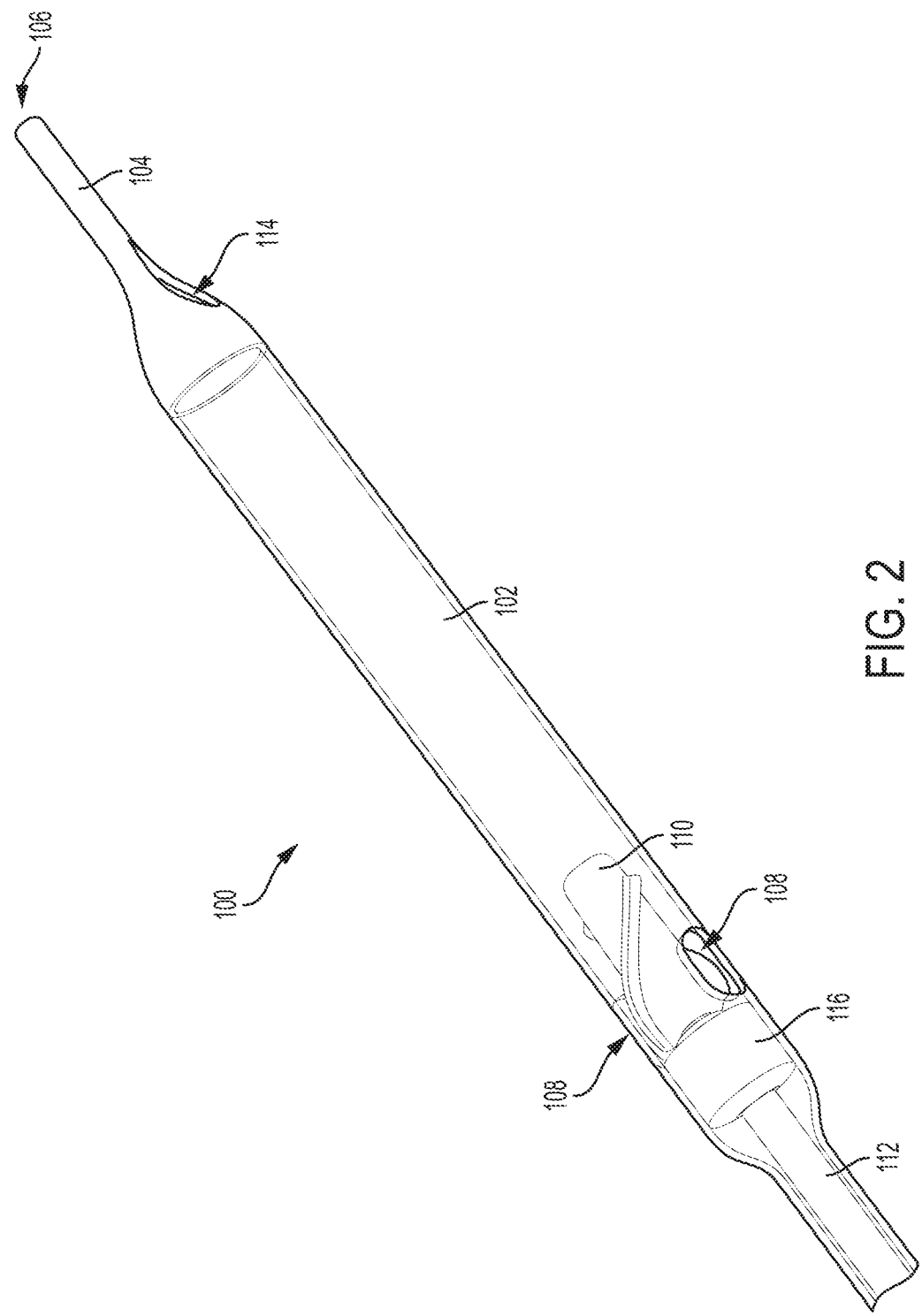
FIG. 2 is a perspective, partially transparent view of a distal portion of another embodiment of a catheter.

FIG. 2 illustrates another embodiment of a catheter 100 that includes at least one restrictor (not shown in FIG. 2 for clarity of illustration). The catheter 100 of FIG. 2 can generally be configured and used similar to that discussed above regarding the catheter 1 of FIG. 1, e.g., include a shaft 102, a soft, distally-tapering atraumatic tip 104, a discharge opening 106, a proximal inlet opening 108, an impeller 110, a drive shaft 112 extending proximally to a motor (not shown), and a distal inlet opening 114. The motor in this illustrated embodiment is external, similar to the embodiment discussed above regarding the catheter 1 of FIG. 1. The proximal inlet opening 108 in this illustrated embodiment is in the form of two opposed ovular openings formed through a sidewall of the shaft 102. The distal inlet opening 114 in this illustrated embodiment is in the form of two opposed ovular openings formed through a sidewall of the atraumatic tip 104 distal to the shaft 102 (one of the openings is obscured in FIG. 2). The catheter 100 can include a bearing 116 just proximal to the impeller 110, which may help stabilize the impeller 110 within the shaft 102.

FIGS. 3-6 illustrate another embodiment of a catheter 200 that includes at least one restrictor (not shown in FIGS. 3-6 for clarity of illustration). The catheter 200 of FIGS. 3-6 can generally be configured and used similar to that discussed above regarding the catheter 1 of FIG. 1, e.g., include a shaft 202, a soft, distally-tapering atraumatic tip 204, a discharge opening 206, a proximal inlet opening 208, an impeller 210, a motor 212, a drive shaft 214 extending between the impeller 210 and the motor 212, and a distal inlet opening 216. The motor 212 in this illustrated embodiment is an on-board motor configured to be implanted with the catheter 200.

Figure 3:
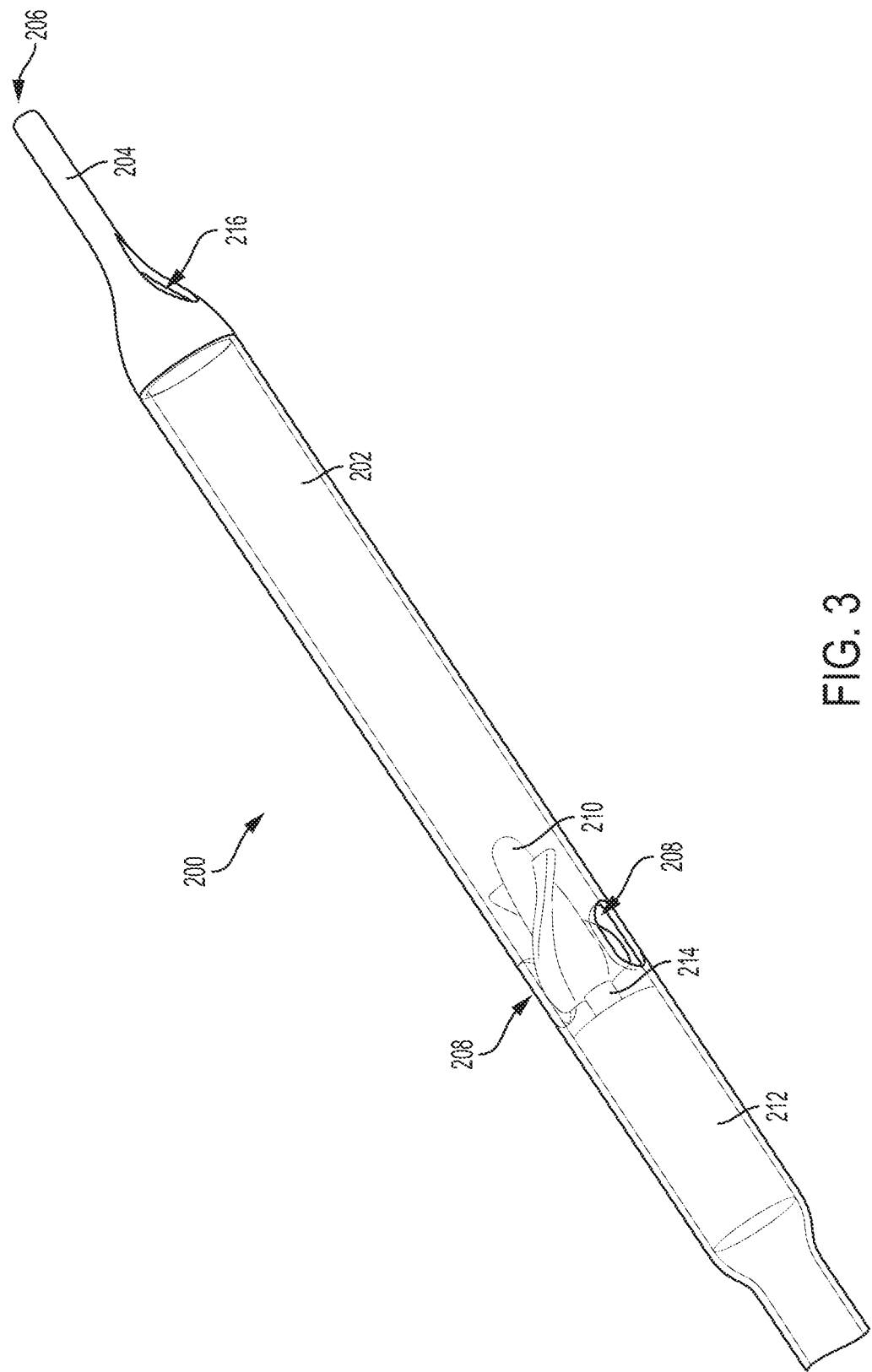
FIG. 3 is a perspective, partially transparent view of a distal portion of yet another embodiment of a catheter.
Figure 4:
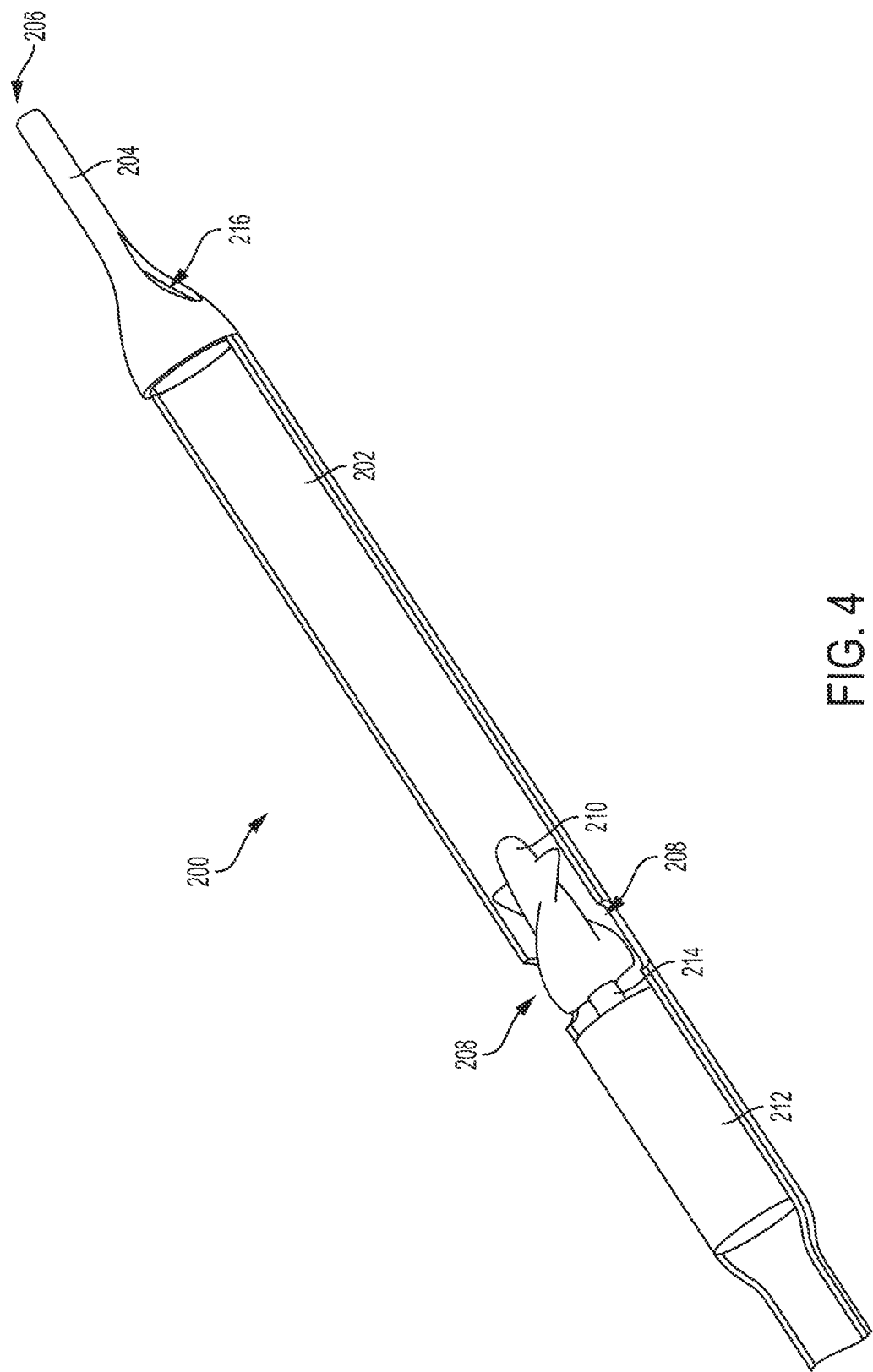
FIG. 4 is a partial cross-sectional view of the distal portion of the catheter of FIG. 3.
Figure 5:
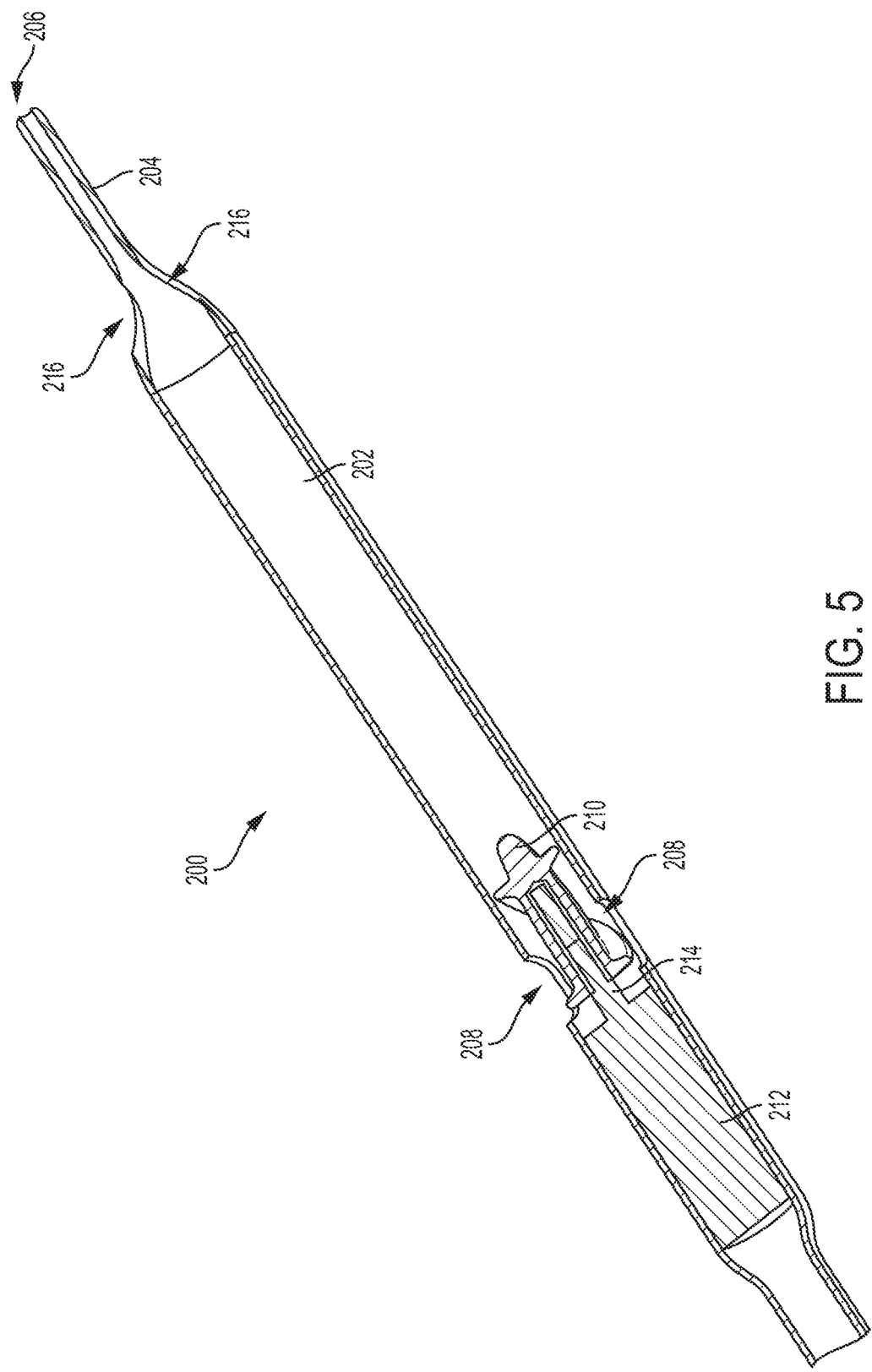
FIG. 5 is a cross-sectional view of the distal portion of the catheter of FIG. 3.
Figure 6:
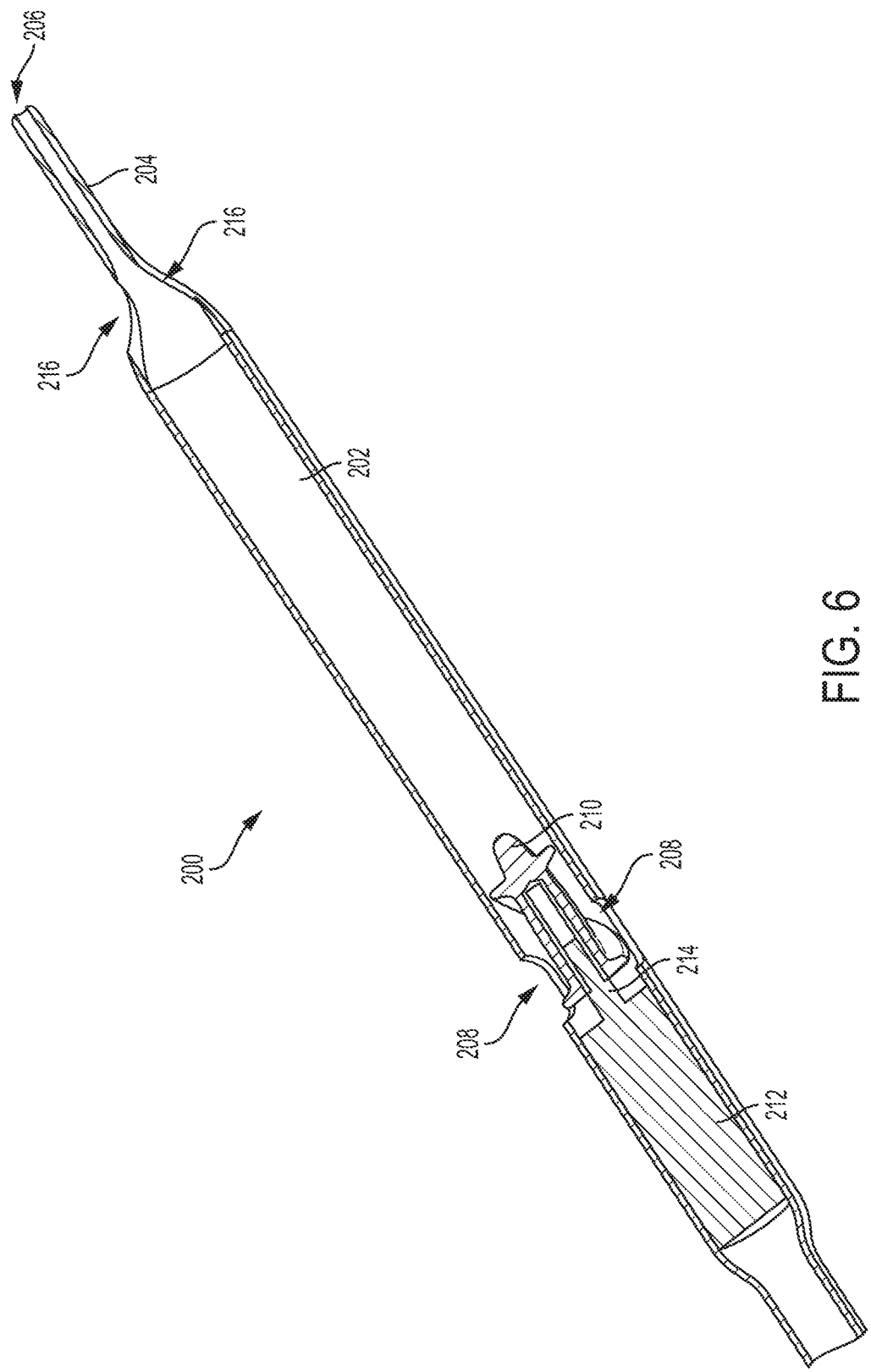
FIG. 6 is a schematic version of the cross-sectional view of FIG. 5.

Similar to the catheter 100 of FIG. 2, the proximal inlet opening 208 in this illustrated embodiment is in the form of two opposed ovular openings formed through a sidewall of the shaft 202, and the distal inlet opening 216 in this illustrated embodiment is in the form of two opposed ovular openings formed through a sidewall of the atraumatic tip 204 distal to the shaft 202 (one of the openings is obscured in FIGS. 3 and 4).

Figure 7:
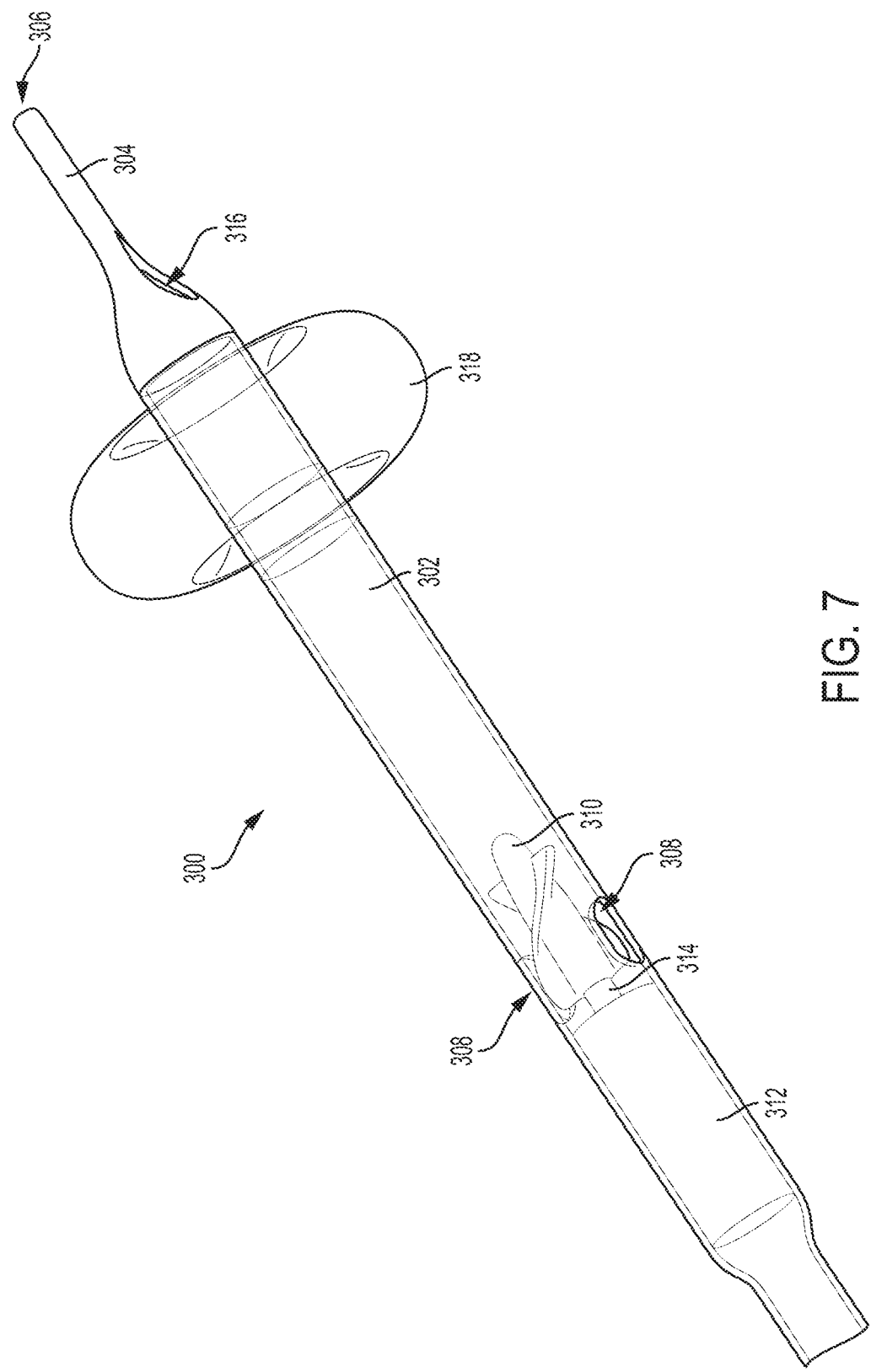
FIG. 7 is a perspective, partially transparent view of a distal portion of yet another embodiment of a catheter.
Figure 8:
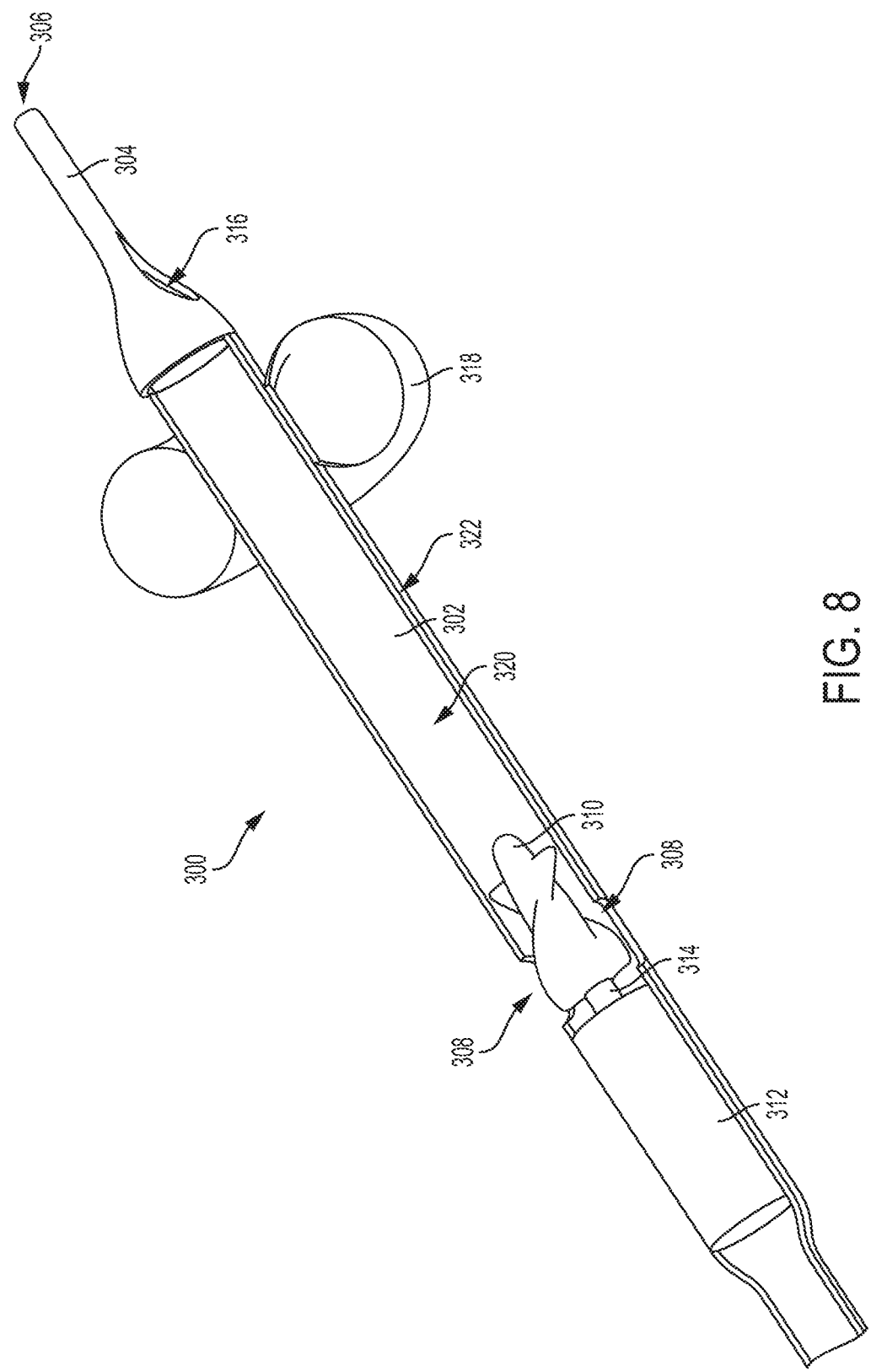
FIG. 8 is a partial cross-sectional view of the distal portion of the catheter of FIG. 7.
Figure 9:
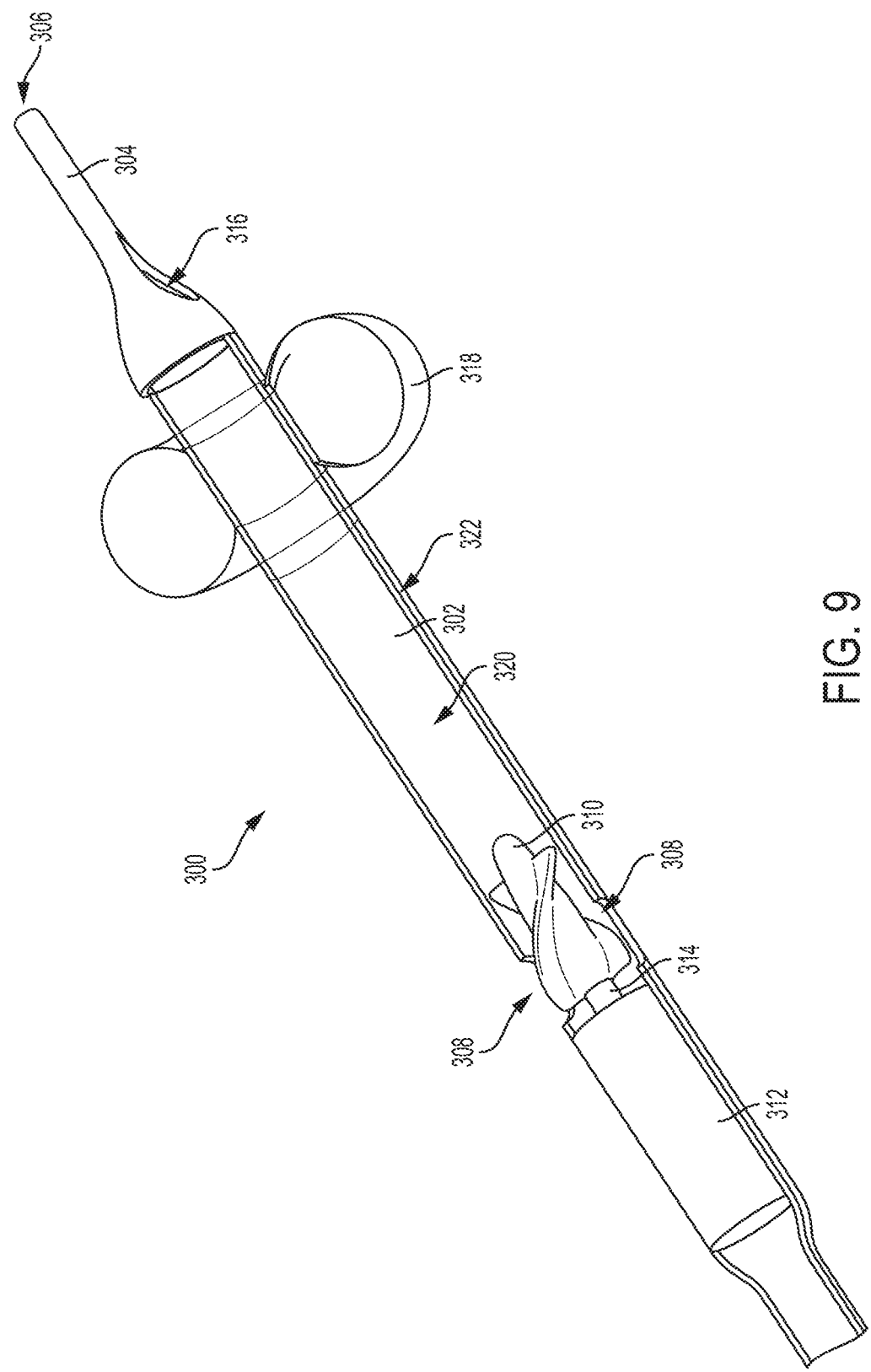
FIG. 9 is a schematic version of the cross-sectional view of FIG. 8.

FIGS. 7-9 illustrate another embodiment of a catheter 300 that includes at least one restrictor 318, which in this illustrated embodiment includes only one restrictor 318 that is located distal to an impeller 310. The catheter 300 of FIGS. 7-9 can generally be configured and used similar to that discussed above regarding the catheter 200 of FIGS. 3-6, e.g., include a shaft 302, a soft, distally-tapering atraumatic tip 304, a discharge opening 306, a proximal inlet opening 308, the impeller 310, an on-board motor 312, a drive shaft 314 extending between the impeller 310 and the motor 312, and a distal inlet opening 316. The shaft 302 includes multiple lumens extending therethrough, including a central lumen 320 for the impeller 310 and the motor 312 and an inflation lumen 322 for inflation/deflation of the restrictor 318, which in this illustrated embodiment includes a balloon. FIGS. 7-9 show the restrictor 318 in an activated configuration, which in this illustrated embodiment is an inflated configuration.

In at least some embodiments, a catheter including restrictors can include a flexible membrane to which the restrictors are appended and which enables fluid (e.g., blood flow) to bypass a low pressure zone defined between the restrictors.

Figure 10:
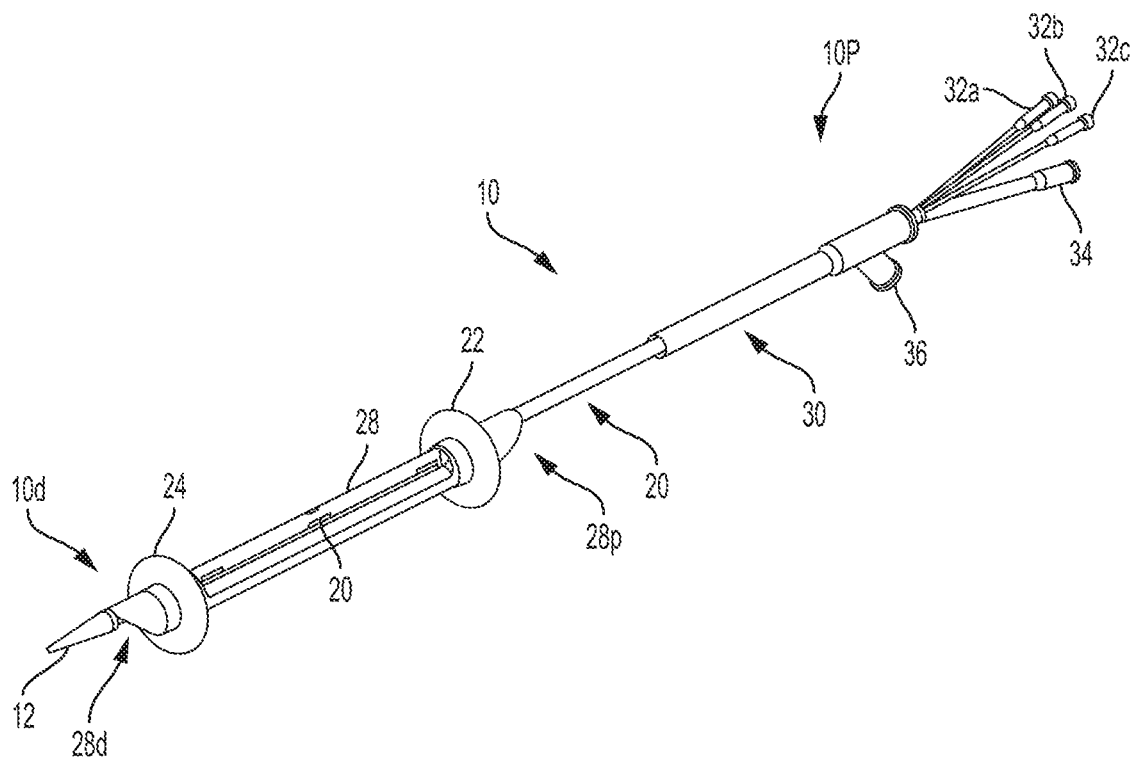
FIG. 10 is a perspective view of one embodiment of a catheter system.

FIG. 10 illustrates one embodiment of an indwelling catheter system 10 that can include a flexible membrane 28 and at least one restrictor 22, 24, which are in the form of balloons in this illustrated embodiment. As illustrated, the indwelling catheter system 10 includes an introducer sheath 30 used to deploy a catheter 20 having a generally elongate tubular shape, with a circular or ovular cross-sectional geometry. The indwelling catheter system 10 can include proximal end 10p, which can be configured to be placed outside of a patient's body, and distal end 10d, which can be configured for placement within a patient's vein.

Figure 10A:
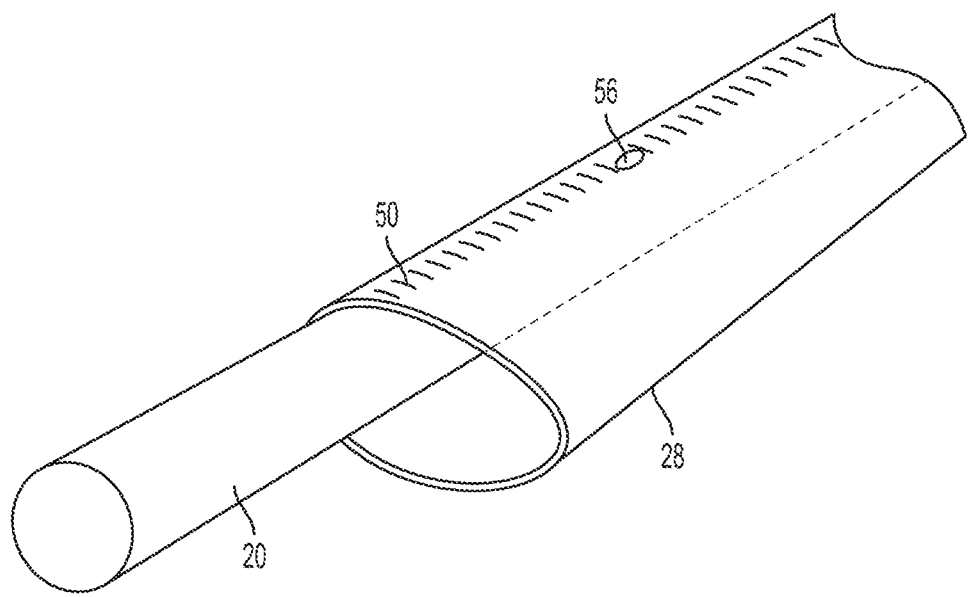
FIG. 10A is perspective view of a flexible membrane and catheter shaft of the catheter system of FIG. 10.
Figure 10B:
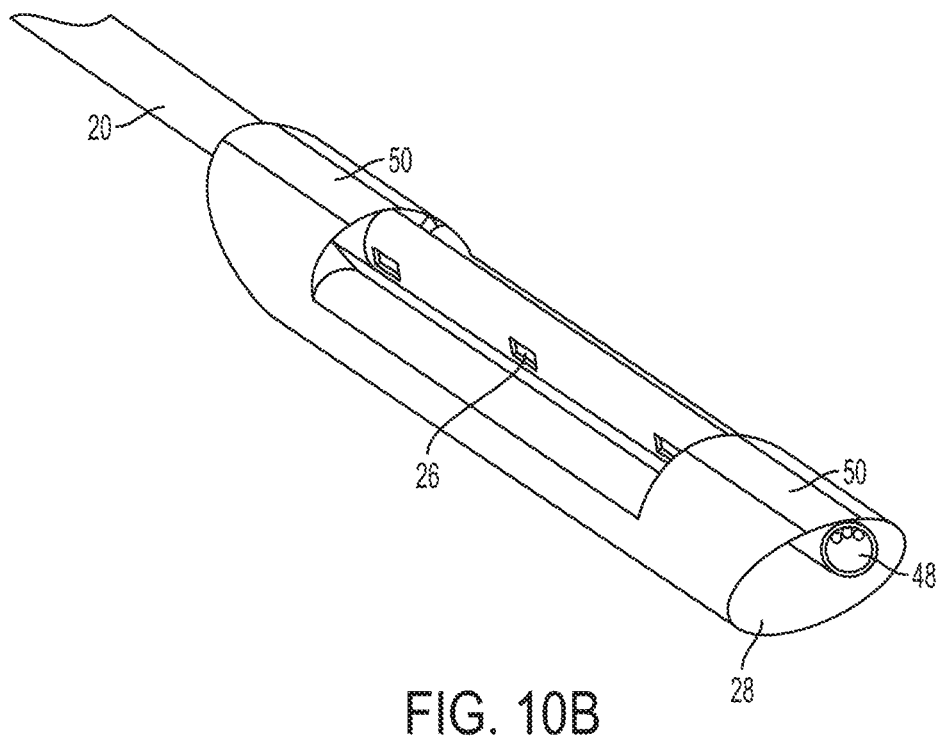
FIG. 10B is another perspective view of the flexible membrane and catheter shaft of the catheter system of FIG. 10A.

The catheter 20 can have a single suction lumen 48 (see FIGS. 14 and 15) for communicating fluid out of the vein to an external pump, the flexible membrane 28 (which is tubular in this illustrated embodiment), and first and second restrictors 22, 24, which are attached to the membrane 28 and surround the membrane 28 and catheter 20. The flexible membrane 28 can be assembled to the catheter 20 (e.g., to the shaft thereof) in any of a number of ways to enable the flexible membrane 28 to form an ovoid or a kidney shape upon expansion of the flexible membrane 28 (as a result of activating the restrictors 22, 24) so that fluid can be transported from a position within the vein proximal to the first restrictor 22, through the low pressure zone within the vein, and to discharge the fluid at a point distal to the second restrictor 24. The flexible membrane 28 can be attached, e.g., bonded or welded, around a partial portion (such as a non-zero portion that is less than 360° of the catheter shaft's circumference 50) or full portion (360° around the catheter shaft's circumference 50) of the circumference 50 of the catheter's shaft, such as in a range of about 10° to 360° of the shaft's circumference 50. FIGS. 10A and 10B illustrate the flexible membrane 28 attached to a partial portion around the catheter shaft circumference 50. At least one inflation port 56 is in fluid communication with an inflation lumen (control lumen 42 discussed further below) for inflating the first restrictor 22 and is disposed on a surface of the flexible membrane 28 and will be underneath the first restrictor 22 attached thereto, as discussed below. A second inflation port (not shown) is in fluid communication with at least one inflation lumen (control lumen 44 discussed further below) for inflating the second restrictor 24 and is disposed on a surface of the flexible membrane 28 and will be underneath the second restrictor 22 attached thereto, as discussed below. As shown in FIG. 10B, which has a portion of the flexible membrane 28 removed for clarity of illustration, at least one suction port 26 is extending through an external surface of the catheter 20 such that it is in fluid communication with a suction lumen 48.

Figure 10C:
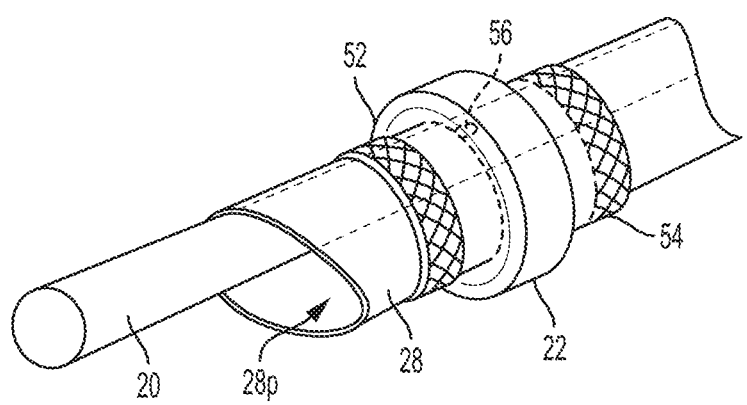
FIG. 10C is a perspective view of a restrictor of the catheter system of FIG. 10 attached to the flexible membrane of the catheter system.
Figure 10D:
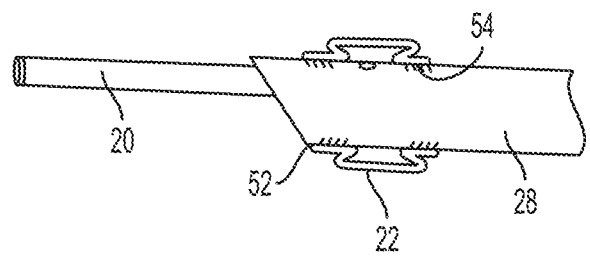
FIG. 10D is side, partial cross-sectional view of flattened edges of the restrictor of FIG. 10A.
Figure 10E:
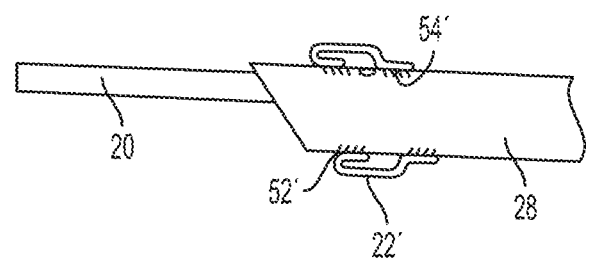
FIG. 10E is a side, partial cross-sectional view of folded edges of another embodiment of a restrictor.

Following attachment of the flexible membrane 28 to the catheter 20, the restrictors 22, 24 can be attached to the catheter 20. As shown in FIG. 10C, the first restrictor 22 can be bonded or welded to an outer surface of the flexible membrane 28 over the inflation port 56 so that the first restrictor 22 surrounds the outer circumference 52, 54, of the catheter 20 and the flexible membrane 28. As shown in FIG. 10D, edges of the first restrictor 22 can be flattened to extend beyond the collapsed balloon and bonded to the flexible membrane 28. The second restrictor 24 can be attached to the catheter 20 similar to the first restrictor's attachment to the catheter 20. In an alternate embodiment, as shown in FIG. 10E, a restrictor 22' has at least one edge 52' thereof folded under and bonded beneath the collapsible tube of the restrictor 22'. One or both of the first and second restrictors 22, 24 can be attached to the catheter 20 similar to the attachment of the restrictor 22' of FIG. 10E.

Figure 10F:
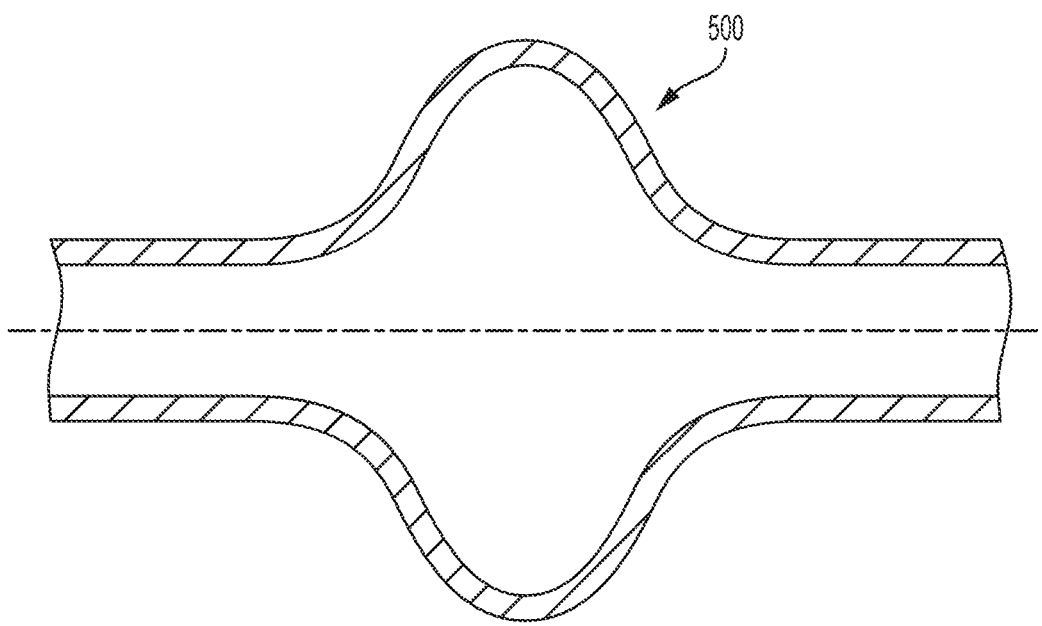
FIG. 10F is a cross-sectional schematic view of one embodiment of a pattern for forming a restriction member with a torus shape.
Figure 10G:
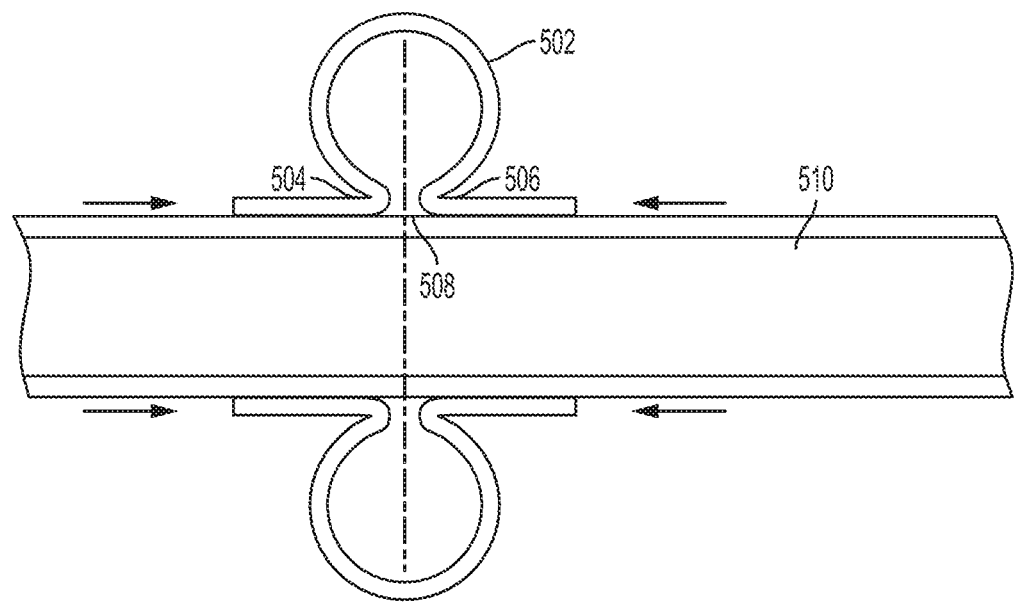
FIG. 10G is cross-sectional schematic view of one embodiment of a restriction member formed using the pattern of FIG. 10F and one embodiment of a sleeve on which the restriction member is assembled.
Figure 10H:
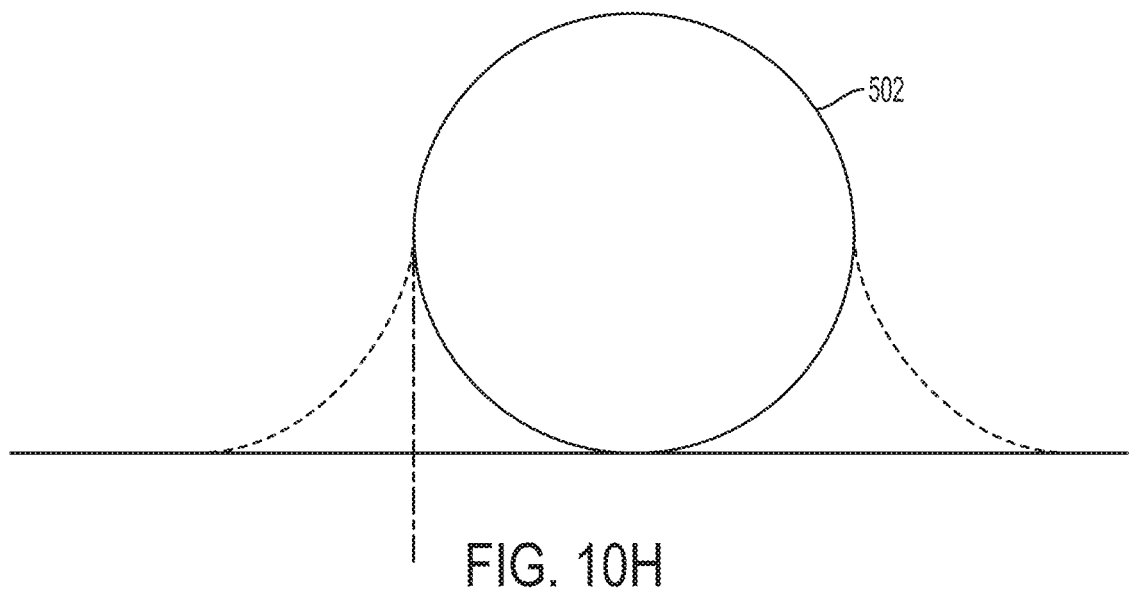
FIG. 10H is a cross-sectional schematic view of the restriction member of FIG. 10G following inversion of legs thereof.

FIGS. 10F-10H illustrate one embodiment of a method for manufacturing a torus-shaped restriction member 502 configured to be attached to a catheter shaft as discussed herein. As shown in FIG. 10F, a pattern 500 is formed by a process such as blow molding or dip molding. For example, a slope of the mold pattern can be formed in a continuous shape without sharp corners or directional reversion. As shown in FIG. 10G, after the restriction member 502 is formed using the pattern 500, it is assembled onto a collapsible sleeve 510. During the assembly, two legs 504, 506 of the restriction member 502 are pushed towards each other and bonded together. The restriction member 502 maintains an opening 508 between the legs 504, 506 to enable the formation or positioning of an inflation port in the catheter that will be used to inflate the restriction member 502. As shown in FIG. 10H, after the legs 504, 506 are brought together, as explained above, a lower section of the restriction member 502 is inverted inward. The curvature of the restriction member 502 is maintained in the opposite direction thereby maintaining material continuity to form the restriction member 502, as illustrated.

The suction lumen 48 can accommodate the flow of fluid from the vein in which the catheter 20 is implanted to a pump external to the patient, when deployed, and the membrane 28 can enable fluid returned from the pump to bypass the portion of the vein occluded by the restrictors 22, 24. As shown in FIGS. 11A, 11B, 14, and 15, the suction lumen 48 can communicate with the suction port 26, formed in an outer wall of catheter 20, and can extend to a proximal end of the catheter 20. The proximal end of the catheter 20 can include a hub 34 which communicates with discharge tubing (not shown) coupled to the pump external to the patient (not shown) to communicate fluid withdrawn from within the low pressure zone between the restrictors 22, 24 through the suction lumen 48 of the catheter 20. Fluid present in the vein in which the catheter 20 is implanted, and between the deployed restrictors 22, 24 of the catheter 20, is drawn from the vein into the suction port 26 and into the suction lumen 48 of catheter 20 so that it can be communicated to the external pump (not shown) via the suction lumen 48 and the discharge tubing.

The tubing extending out of the pump (not shown) to return fluid to the catheter system 10 can be coupled to the sheath 30 at a discharge port 36 (see FIGS. 10, 12A, 12B, and 13). Fluid returned from the pump will enter the discharge port 36 and be discharged within the vein external to the catheter 20. The pump can facilitate fluid movement from the catheter 20 through the suction lumen 48 and into the discharge tubing through which it is communicated to the pump. The discharge port 36 can be configured to connect to an end of the drainage tubing having its other end in fluid communication with the pump. The discharge port 36 can, as shown, include surface features formed thereon and extending therearound to facilitate its connection to the discharge tubing.

As shown in FIGS. 10, 10A, 11A, and 11B, the first restrictor 22 can be downstream of (e.g., distal to) a proximal opening 28p of the membrane 28, and a distal opening 28d of the membrane 28 can be downstream of second restrictor 24. Thus, when the first and second restrictors 22, 24 are activated or deployed to fully occlude the vein, the lumen of the membrane 28 can provide a bypass route for fluid (e.g., blood) returning from the external pump or otherwise flowing downstream within the vein external to catheter 20. In other words, even though the vein is occluded by the restrictors 22, 24, blood and other fluid can flow through the lumen of the membrane 28 to flow from a position upstream of (e.g., proximal to) the proximal restrictor 22 to a position downstream of the distal restrictor 24. Although the catheter 20 and the flexible membrane 28 are illustrated to be oriented in a side-by-side relationship with respect to one another, they can be oriented in any other suitable manner, including having one member disposed within the other member. Also, the catheter 20 can have any number of additional lumens, which can function, for example, as control lumens to facilitate activation of the restrictors 22, 24 and/or to sense pressure at various locations within the vein in which the catheter 20 is disposed.

The catheter 20 can include a distal atraumatic tip 12 that can facilitate placement of the catheter 20 into the vein of a patient. The distal atraumatic tip 12 can have an aperture such that the tip 12 has a lumen extending therethrough. The lumen of the tip 12 can be configured to allow passage of a guide wire through the tip 12. The catheter 20, including the flexible membrane 28 and the restrictors 22, 24, can be advanced over the guide wire to be deployed from the sheath 30. The lumen and the aperture can be sized to accommodate a standard guide wire of size such as about 0.014", about 0.018", about 0.035", or about 0.038". In addition to or instead of the catheter 20 including the distal atraumatic tip 12, the sheath 30 can include a distal atraumatic tip to facilitate advancement of the sheath 30 having the catheter 20 disposed therein to a location where the catheter 20 is to be released from (e.g., advanced distally out of) the sheath 30. The sheath's distal atraumatic tip can include a lumen to allow passage of a guide wire through the tip, as discussed above.

Figure 11A:
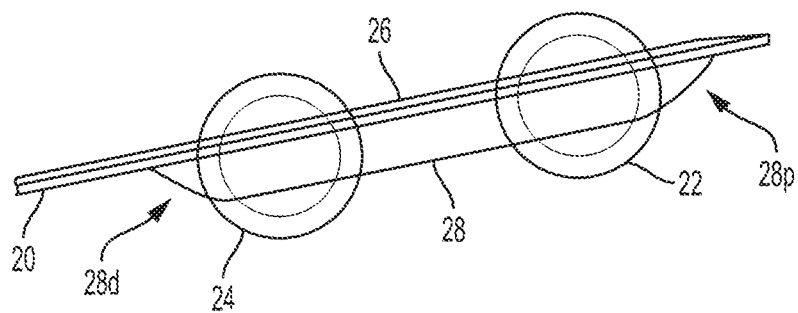
FIG. 11A is a perspective view of a distal portion of the catheter system of FIG. 10.
Figure 11B:
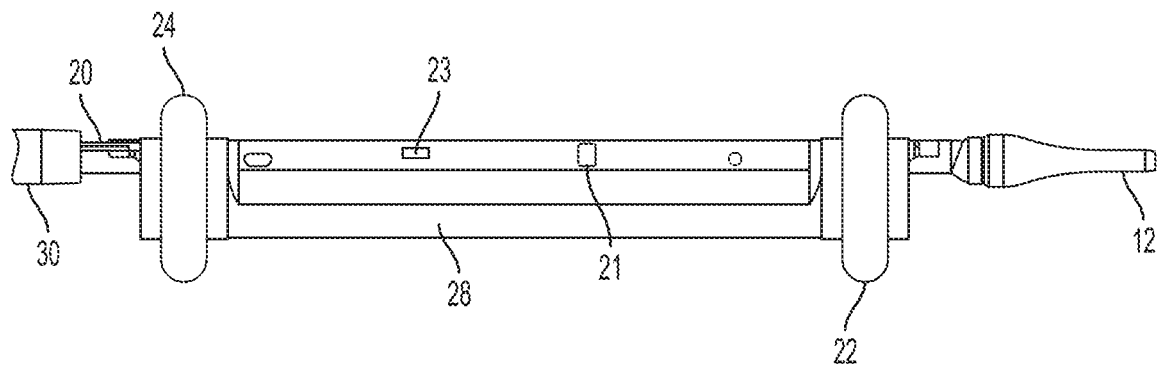
FIG. 11B is a side view of another distal portion of the catheter system of FIG. 10.

As shown in FIG. 11B, the catheter 20 can include one or more radiopaque markers 21 configured to be visible using an imaging technique such as fluoroscopy. As also shown in FIG. 11B, the catheter 20 can include one or more sensors 23, which in this illustrated embodiment includes an optic pressure transducer, located between the restrictors 22, 24 and hence within a low pressure zone created therebetween. The pressure transducer 23 is configured to continually monitor pressure within the low-pressure zone so pump function can be adjusted if necessary to keep the pressure at a desired level (in a desired range of about 2 to 5 mmHg, etc.) and at the location of the discharge lumen so internal jugular vein pressure can be monitored. The pressure transducer 23 is also configured to provide CVP measurements when the restrictors 22, 24 are deflated.

Figure 12A:
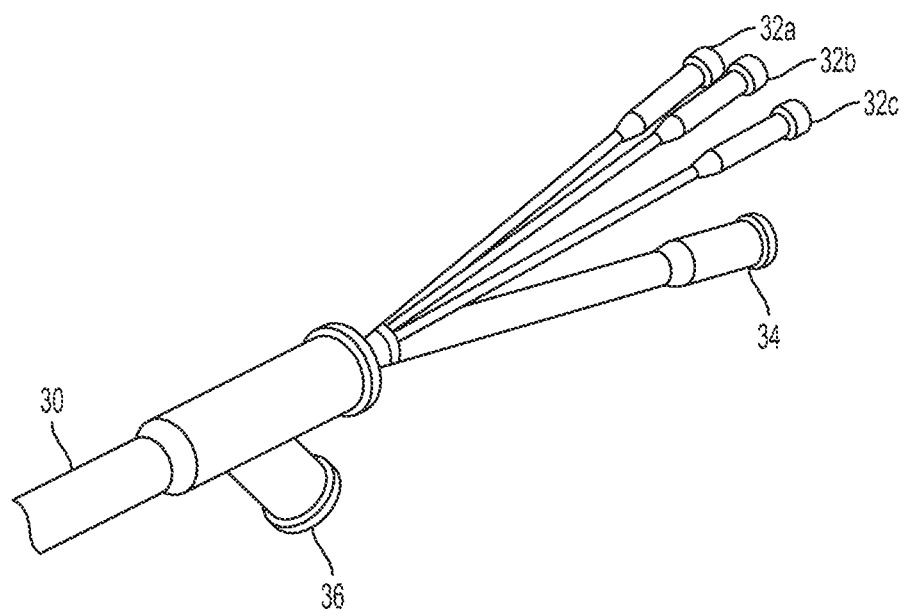
FIG. 12A is a perspective view of a proximal portion of the catheter system of FIG. 10.
Figure 12B:
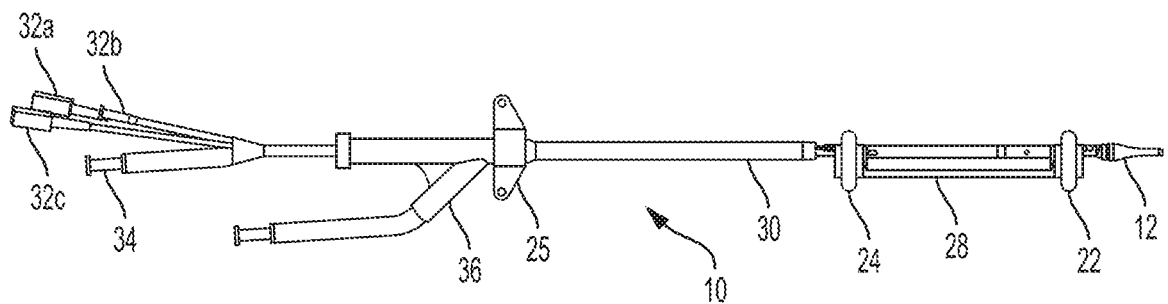
FIG. 12B is a side view of the catheter system of FIG. 10.

As shown in FIG. 12B, the catheter system 10 can include an eyelet 25 configured to facilitate securement of the system 10 to a patient during use. For example, the eyelet 25 can be secured by a suture to the patient's skin. The catheter shaft can be locked in position relative to the sheath 30 using, for example, a Tuohy Borst valve, such that the catheter 20 can be secured to the patient during use via the sheath 30. The eyelet 25 may thus be secured to the patient after the catheter 20 has been advanced through the sheath 30 to be in a desired position within the patient to help ensure that the system 10 is secured to the patient with the catheter 20 in its desired position.

Figure 13:
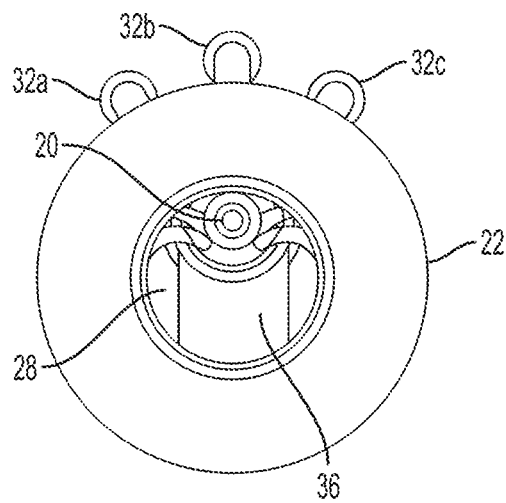
FIG. 13 is a distal end view of the catheter system of FIG. 10.
Figure 14:
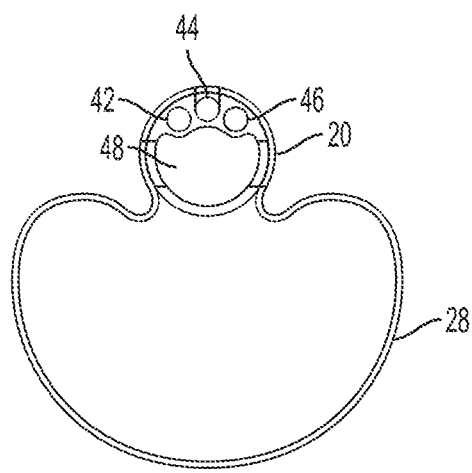
FIG. 14 is a cross sectional view of the catheter system of FIG. 10 with a flexible membrane of the catheter system in an expanded configuration.
Figure 15:
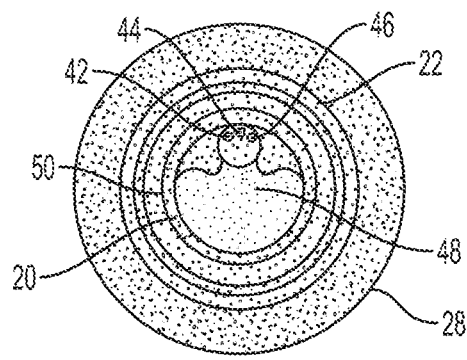
FIG. 15 is a cross sectional view of the catheter system of FIG. 10 having a restrictor thereof in an activated configuration.
Figure 16:
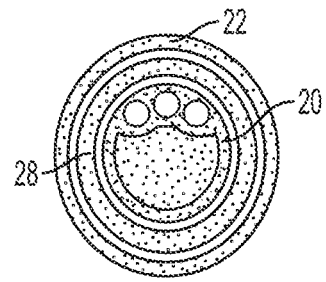
FIG. 16 is a cross sectional view of the catheter system of FIG. 10 having a restrictor thereof in a relaxed configuration.

As shown in FIGS. 10, 12, and 13, the sheath 30 can include a plurality of ports 32a, 32b. 32c in fluid communication with respective ones of a plurality of control lumens 42, 44, 46 within the catheter 20. As shown in FIGS. 14-16, the first and second ports 32a. 32b respectively communicate with the first and second control lumens 42, 44, which can be configured to deliver fluid to the first and the second restrictors 22, 24, respectively, to control the activation and deactivation of the restrictors 22, 24. The third port 32c can communicate with the third control lumen 46, which can communicate with an opening in the catheter 20 for purposes of sensing a pressure within the vein, as discussed above. The third control lumen 36 includes one or more pressure sensors in this illustrated embodiment, but any one or more of the control lumens 42, 44, 46 can include one or more pressure sensors, to be used for sensing pressure at various locations along the vein in which the catheter 20 is implanted, such as between the proximal and distal restrictors 22, 24 and upstream of the proximal restrictor 22.

As shown in FIGS. 14 and 15, the suction lumen 48 is internal to the catheter 20 and the flexible membrane 28 that is external to the catheter 20 and is oriented in a side-by-side arrangement with respect to the catheter 20. The control lumens 42, 44, 46 can be disposed within the catheter 20, such as within the wall of the catheter 20, as shown. As indicated above, the cross-sectional arrangement of catheter 20 can take various forms, and the relative positioning of the suction lumen 48 and the control lumens 42, 44, 46 can vary. More or fewer suction lumens 48 and control lumens 42, 44, 46 can be provided in the catheter 20. For example, one or more additional control lumens can accommodate a variety of non-pressure sensors, as discussed above.

Sizes of the catheter 20, the sheath 30, and the flexible membrane 28 can vary depending upon the catheter system's intended uses. Generally, the catheter 20 can have a length in the range of about 25 to 40 cm. In addition, the diameter can also vary, but suitable catheters will typically be in the range of about 8 to 18 Fr. Other catheters described herein can have a similar size, e.g., a length in the range of about 25 to 40 cm and a diameter in the range of about 8 to 18 Fr. The sheath 30 can have a length in the range of about 10 to 25 cm, can have an internal diameter in the range of about 2.5 to 5.5 mm, and can have an external diameter in the range of about 3 to 6 mm. In one embodiment, the catheter 20 can have a diameter of about 8 Fr and the sheath 30 can have a diameter of about 11 Fr. The flexible membrane 28 can have a length in the range of about 50 to 150 mm. A distance between the distal end of the sheath 30 and the proximal end of the flexible membrane 28 can be up to about 100 mm. The diameter of the control lumens 42, 44, 46 can vary depending upon the requirements of a given application. The suction lumen 48 can have a diameter in the range of about 1 to 4 mm, while pressure inflation lumens can have a diameter in the range of about 0.1 to 1 mm.

Figure 17A:
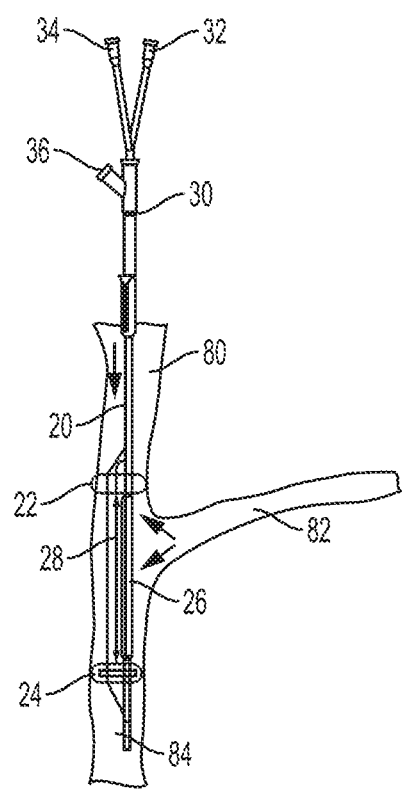
FIG. 17A is a schematic, partially cross-sectional view of a portion of the catheter system of FIG. 10 implanted in a patient.
Figure 17B:
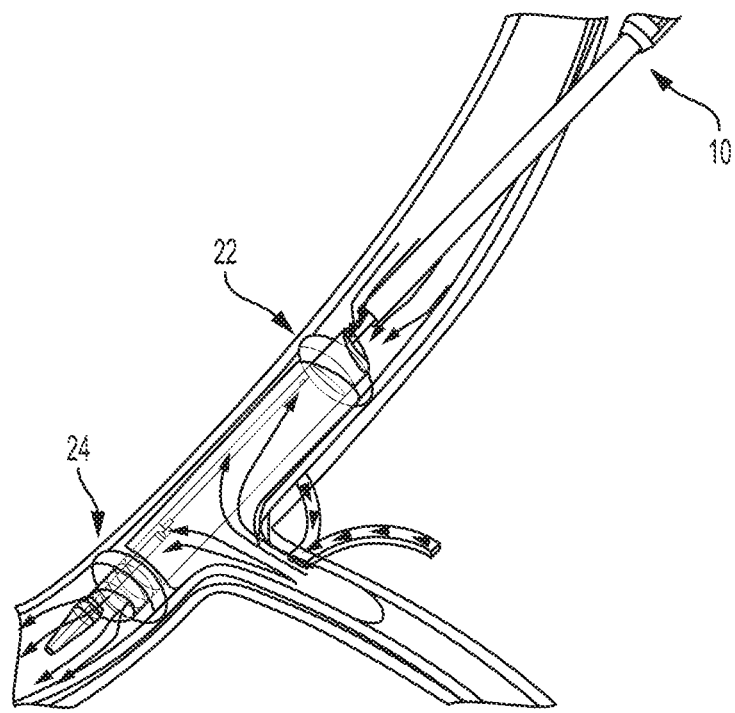
FIG. 17B is a perspective, partially cross-sectional view of another portion of the catheter system of FIG. 17A implanted in the patient.
Figure 17C:
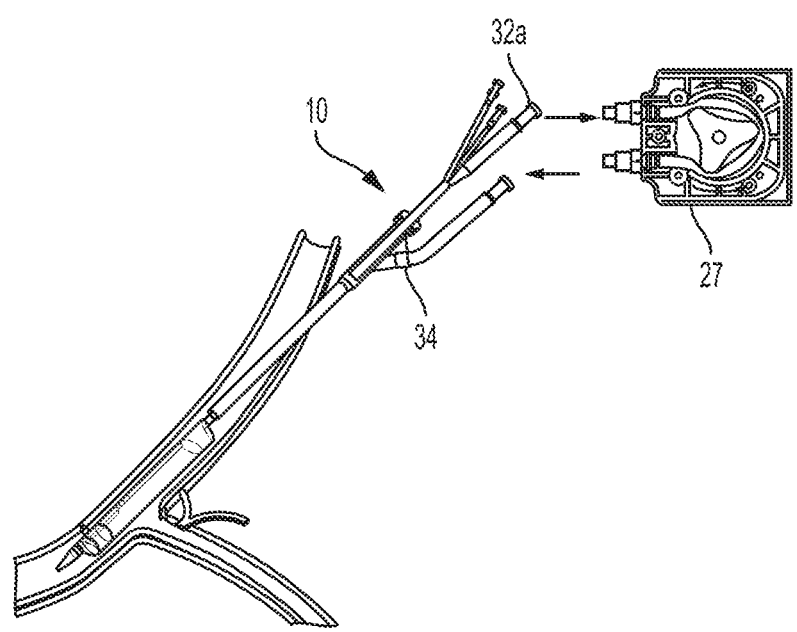
FIG. 17C is another perspective, partially cross-sectional view of the catheter system of FIG. 17A implanted in the patient.

FIGS. 17A-17C illustrate one example of the catheter 20 implanted within a patient, in particular within a jugular vein 80 of the patient. FIG. 17B also illustrates a location of the low pressure zone and illustrates fluid flow through the catheter 20 as indicated by two sets of arrows into and one set of arrows out of the catheter 20. FIG. 17C also illustrates one embodiment of a pump 27, a peristaltic pump (such as a peristaltic blood pump motor model DriveSure™ 48 VDC. Head model 520RL2, available from Watson Marlow), configured to pump fluid in and out of the catheter system 10 via the ports 32a, 34. As shown, the first restrictor 22, which in this illustrated embodiment is positioned at a region of the catheter 20 that is proximal to the suction port 26 and that marks the proximal or upstream boundary of the low pressure zone, can be positioned proximal to (upstream of) a point at which the patient's subclavian vein 82 enters the jugular vein 80. The second restrictor 24, which in this illustrated embodiment is positioned distally of the first restrictor 22 and between the suction port 26 and the distal end of the catheter 20, can be positioned distal to (downstream of) the point at which the subclavian vein 82 enters the jugular vein 80, and the second restrictor 24 can be in the patient's innominate vein 84. Alternatively, the catheter 20 can treat both lymphatic ducts by placing the first restrictor 22 proximal to (upstream of) the point at which the subclavian vein 82 enters the jugular vein 80 and placing the second restrictor 24 distal (downstream of) to the point at which both of the patient's innominate veins enters the subclavian vein 82. Alternatively, the second restrictor 24 can be positioned in the subclavian vein 82.

The catheter 20 can be positioned with the jugular vein 80 as shown in FIGS. 17A and 17B in any of a variety of ways. For example, the positioning can be conducted using a 12 Fr sheath 30 to puncture the venous wall. The sheath 30 can be advanced into the vein 80 with the catheter 20, the flexible membrane 28, and the restrictors 22, 24 collapsed and contained therein. After insertion of the sheath 30, the catheter 20 along with the flexible membrane 28 and the restrictors 22, 24, can be advanced through the distal tip of the sheath 30 and positioned downstream of the sheath 30. Alternatively, the sheath 30 can be introduced first, and then the catheter 20 can be introduced by being advanced through the sheath 30. Regardless of whether the sheath 30 and the catheter 20 are introduced sequentially or simultaneously, the catheter 20 can be configured to be removed from the sheath 30 at any time. If at any time throughout a procedure there might be a question with regards to the integrity of the catheter 20, the catheter 20 being removable with the sheath 30 remaining in place within the patient allows the catheter 20 to be replaced with a new one introduced into the sheath 30 or for the catheter 20 to be re-introduced into the sheath 30 if the catheter's integrity is deemed acceptable.

The distal restrictor 24, when activated, isolates the incoming blood flow from the subclavian and jugular veins 82, 80 from the blood flow of the innominate vein 84 and ensures that all incoming blood is directed to the pump 27. The proximal restrictor 22, when activated, isolates the blood flow from the jugular vein 80 and ensures that all blood flow from a position upstream of the proximal restrictor 22 is transported through the flexible membrane 28. The pump is activated to maintain the jugular and innominate vein pressure and thus the nominal blood flow. The proximal restrictor 22, when activated, directs the blood flow from the jugular vein 80 and from the discharge port 36 within the sheath 30 down to the innominate vein 84. Actuation of the pump helps to create a low pressure zone in the vicinity of the junction of the jugular vein 80 and the subclavian vein 82 by withdrawing fluid in this region, recirculating it through the pump, and discharging the fluid upstream of this region through the sheath 30. Because the outflow of the thoracic and lymphatic ducts is located in this region, the lower pressure will facilitate drainage of lymphatic fluid.

Figure 18:
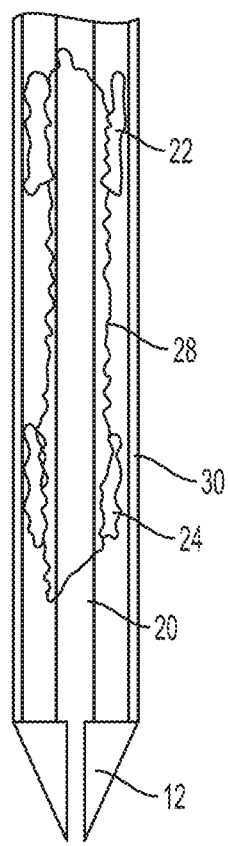
FIG. 18 is a side cross-sectional view of a distal portion of the catheter system of FIG. 10.
Figure 19:
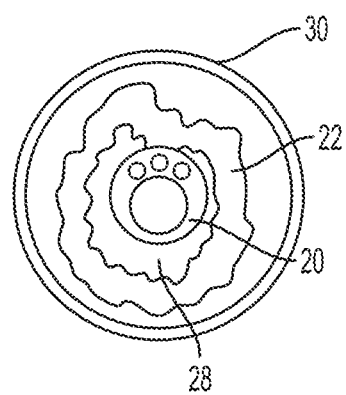
FIG. 19 is a cross-sectional view of the distal portion of the catheter system of FIG. 18.
Figure 20:
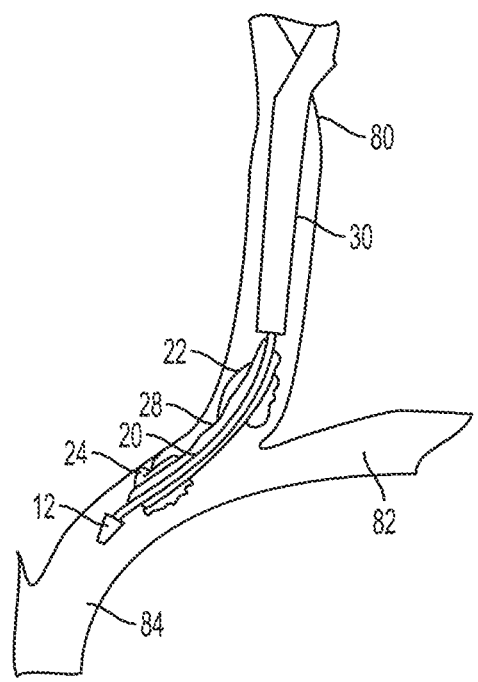
FIG. 20 is a schematic, partially cross-sectional view of a distal portion of the catheter system of FIG. 10 introduced into a vein.

The catheter 20 can be implanted in the jugular vein 80 as shown in FIGS. 17A and 17B in any of a variety of ways. FIGS. 18-20 illustrate one embodiment of implanting the catheter 20 can be implanted in the jugular vein 80. The catheter 20 can be similarly implanted in another vein, and other catheters described herein can be implanted in a vein similar to that discussed with respect to FIGS. 18-20.

FIGS. 18 and 19 illustrate the indwelling catheter system 10 (only a distal portion thereof is shown in FIG. 18) in an initial configuration in which the catheter 20 is disposed within the sheath 30 in a compressed configuration. In the initial configuration, the sheath 30 can have the catheter shaft 20 positioned therein, encircled by a compressed flexible membrane 28 further surrounded by compressed restriction members 22, 24.

A distal portion of the indwelling catheter system 10, e.g., a distal portion of the sheath 30, in the initial configuration can be inserted into the jugular vein 80 of the patient, which is the right internal jugular vein in this illustrated embodiment. A proximal portion of the indwelling catheter system 10. e.g., a portion including the ports 32, 34, 36, can remain outside the body of the patient to facilitate access to the ports 32, 34, 36. With the distal portion of the catheter system 10 at the target site (e.g., within the vein in which the catheter 20 is to be implanted), the catheter 20 can be advanced out of the sheath 30, as shown in FIG. 20, such that a proximal portion thereof is positioned within the jugular vein 80 and a distal portion thereof is positioned within the SVC 84. The suction port 26 disposed between the first and second restriction members 22, 24 enables suction of blood deposited within the low pressure zone from the subclavian vein 82 and from the innominate vein 84. Such arrangement enables drainage of both the patient's right lymphatic duct and thoracic duct. After positioning of the catheter 20 within the patient, the first and second restrictors 22, 24 can be expanded. e.g., moved from their relaxed configuration to their activated configuration, as shown in FIGS. 17A and 17B. The expansion of the restrictors 22, 24 also expands the flexible membrane 28. e.g., moved the flexible membrane 28 from a relaxed configuration to an activated configuration. As mentioned above, the restrictors 22, 24 can be expanded simultaneously or sequentially. As mentioned above, the expansion of the restrictors 22, 24 isolates a portion of the vein 80 in which the catheter 20 is deployed from a surrounding area, and, thus, an area (e.g., a low pressure zone) proximate to the thoracic duct is isolated and fluid can be removed via the suction port 26 positioned on the catheter 20 located within the isolated area.

The catheter system 10 discussed above is configured to pump blood out of a patient's body and back into the body. A catheter system can instead include an impeller, such as in the catheter embodiments of FIGS. 1-6, such that blood need not be pumped out of and back into a patient's body and features of the catheter system 10 related thereto need not be included (e.g., a pump, a discharge port, and related tubing need not be included). The catheter system including an impeller can otherwise be similar to the catheter system 10, e.g., include a flexible membrane, include a sheath, etc.

The catheters described herein can be used in a variety of surgical methods, including surgical methods for treating pulmonary edema. The method can include verifying a location of the patient's thoracic duct and/or the patient's lymphatic duct, which can help a surgeon and/or other medical professional involved in performing a surgical procedure that includes implanting the catheter verify that the restrictor(s) of the catheter are implanted in the correct location within the patient. The verification can be performed in any of a variety of ways, as will be appreciated by a person skilled in the art, such as by using an imaging technique such as echo or fluoroscopy. In an exemplary embodiment, the verification can include advancing a set of pig tailed wires into the patient's subclavian or jugular veins and advanced toward a junction of the jugular and subclavian veins. Once one of the pig tailed wires enters the lymphatic duct or the thoracic duct, that one of the pig tailed wires can open itself inside the duct it entered, e.g., due to a default expanded configuration of the wire. The pig tailed wires can include, for example, a default expanded circle size of 4 cm. The location of the entered duct can be verified using an imaging technique that visualizes the expanded wire therein.

The verification can occur after the implantation of the catheter such that the implanted location of the catheter can be determined in view of the verification and adjusted if need be in view of the verification. Additionally or alternatively, the verification can be performed prior to the implantation of the catheter. Similarly, the verification can be performed prior to and/or after the restrictor(s) are moved from the relaxed configuration to the activated configuration to verify the position(s) of the restrictor(s), and the verification can be performed prior to and/or after one or more sensors are implanted in the to verify that the sensor(s) are desirably positioned. As discussed above, the sensor(s) in some embodiments are not implanted and are instead located outside the patient's body, and/or at least one sensor is implanted and at least one sensor is located outside the patient's body. Various embodiments of positioning tubes such as catheters is further described in U.S. Patent Publication No. 2015/0343136 entitled "System And Method For Treating Pulmonary Edema" filed Feb. 19, 2015, which is hereby incorporated by reference in its entirety.

With the catheter implanted, the restrictor(s) in the activated configuration, and, if being used in the system, the sensor(s) positioned, fluid flow can be controlled with the pump. The control can generally occur as described above. In at least some embodiments, controlling the pump can include continuously running the pump. In at least some embodiments, controlling the pump can include periodically running the pump. In periodically running the pump, the pump can default to an idle state in which the pump is not pumping fluid. For example, in response to receipt of a user input requesting pumping, e.g., input by a user to an I/O device in electronic communication with the pump via a controller, input wirelessly to the pump, etc., the pump can be actuated so as to run and pump fluid. The pump can continue pumping until occurrence of a stop condition. Examples of the stop condition include a predetermined amount of time passing after the pump starts running and a second user input being received that requests pumping to stop. In response to the stop condition occurring, the pump can be actuated to return to its idle state. For another example, in response to sensing a particular parameter value (e.g., a particular pressure value, etc.) with one or more sensors, the pump can be actuated so as to run and pump fluid or the pump can be stopped so as to stop pumping fluid. The parameter can continue being measured with the one or more sensors, thereby allowing the pump to be controlled in real time in response to measured values.

In at least some embodiments, a control module can be configured to control the operation of a system including a catheter. For example, for a system configured to treat pulmonary edema, the system can include a control module to receive information from sensor(s) of the system, to activate restrictor(s) of the system, and adjust a flow rate of a pump of the system. Upon receiving information from the sensor(s), the control module can be configured to actuate the pump function. The control module can further be configured to process information received from the sensor(s) to alter restriction volume, such as an inflation amount of each of the system's one or more restrictors. In at least some embodiments, the system can include a plurality of sensors and the control module can be configured to receive information from at least one of the sensors regarding pressure within a jugular vein of a patient, information from at least one of the sensors regarding pressure at the bifurcation of the patient's jugular and subclavian veins, and information from at least one of the sensors regarding pressure at the patient's innominate vein. Embodiments of a control module include the motor/controller 9 of FIG. 1, a control module 600 of FIG. 21, a control module of FIG. 22, and a control module 826 of FIG. 26.

Figure 21:
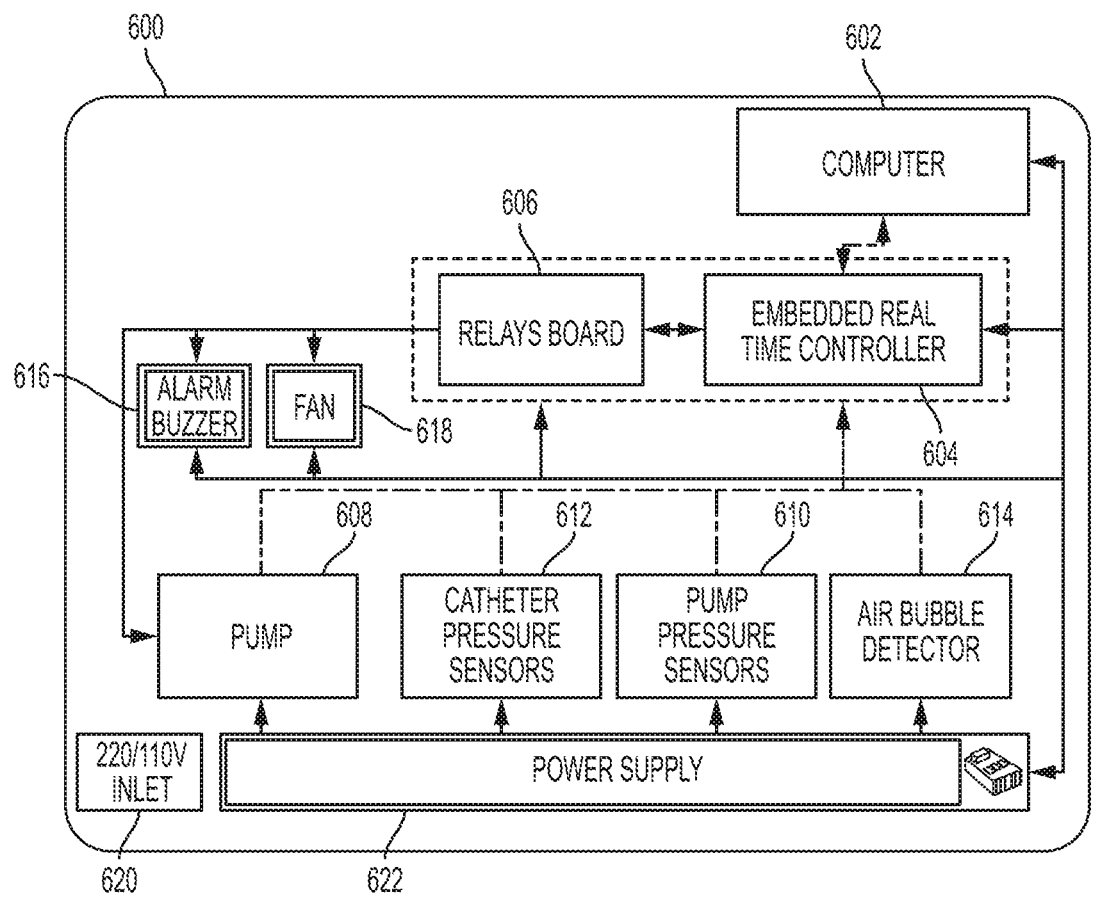
FIG. 21 is a schematic diagram of one embodiment of a control module.

The control module 600 of FIG. 21 includes a computer (e.g., a PC, etc.) 602, a controller 604 in the form of an embedded real time controller, a safety relays board 606, a pump 608 in the form of a peristaltic pump, pump pressure sensors 610 that include a pump inlet pressure sensor and a pump outlet pressure sensor, catheter pressure sensors 612 that include a first catheter pressure sensor configured to be positioned in a jugular vein of a patient and a second catheter pressure sensor configured to be positioned in a subclavian vein of the patient, an air bubble detector 614, an alarm notification mechanism 616 in the form of an alarm buzzer, a fan 618 configured to provide cooling for safety, an electrical inlet 620, and a power supply 622 in the form of an AC to DC power supply. The control module 600 can also include a drip chamber (not shown) configured to allow gas (e.g., air) to rise out of blood flowing through the control module 600 before the blood returns to the patient to facilitate patient safety. The computer 602 is shown as part of the control module 600 in this illustrated embodiment, but the computer 602 can be a separate component from the control module 600 and instead be coupled thereto electronically (wired or wireless).

The computer 602 is configured to act as a control panel for a user to monitor patient and pump parameters so the user can make decisions regarding patient care. The computer 602 includes a user interface on a display thereof to facilitate providing of the parameters to the user. The computer 602 is configured to provide on the user interface identified safety-related concerns, such as air bubbles detected by the air bubble detector 614, and/or to cause the notification mechanism 616 to provide notification of the identified safety-related concerns to the user, such as by buzzing the alarm buzzer, by illuminating a light coupled to the control module 600, by sending an electronic message such as an email or a text message to the user, by showing a message on the computer's display, etc.

The computer 602 is configured to receive real time information from various components of the control module 600, via the real time controller 604, which may facilitate control of the catheter system that includes the control module 600, facilitate providing notice to a user of system functionality, and/or facilitate collection of data for later analysis for patient treatment purposes. The user notification allows the user to take one or more corrective actions to address the subject matter of the notification, such as adjusting a speed of the pump 608, deflating restrictor(s) of the catheter system to allow catheter removal, powering off the control module 600, etc. For example, the computer 602 receives real time pump outlet pressure information from the pump outlet pressure sensor 610 to allow the computer 602 to determine whether the pump outlet pressure is within a pre-programmed acceptable safe range and, if not, to adjust a speed of the pump 608 to urge the pump outlet pressure to be within the safe range and/or cause a user notification to be provided indicating a possible unsafe pressure situation. For another example, the computer 602 receives real time pump inlet pressure information from the pump inlet pressure sensor 610 to determine whether the pump inlet pressure is within a pre-programmed acceptable safe range and, if not, to adjust a speed of the pump 608 to urge the pump inlet pressure to be within the safe range and/or cause a user notification to be provided indicating a possible unsafe pressure situation. For yet another example, the computer 602 receives real time jugular vein pressure information from the first catheter pressure sensor 612 to determine whether it is within a pre-programmed acceptable safe range and, if not, to adjust a speed of the pump 608 to urge the jugular vein pressure to be within the safe range and/or cause a user notification to be provided indicating a possible unsafe pressure situation. For still another example, the computer receives subclavian vein pressure information from the second catheter pressure sensor 612 to determine whether it is within a pre-programmed acceptable safe range and, if not, to adjust a speed of the pump 608 to urge the subclavian vein pressure to be within the safe range and/or cause a user notification to be provided indicating a possible unsafe pressure situation. For another example, the computer 602 receives air bubble information from the air bubble detector 614 to determine if blood being pumped by the pump 608 includes an amount of air bubbles over a predetermined threshold level and, if so, adjust a speed of the pump 608 to reduce the level of air bubbles and/or cause a user notification to be provided indicating a possible thrombosis risk due to air bubble presence. For yet another example, the computer 602 receives pump rotation information from a pump tachometer coupled to the pump 608 to determine whether the pump 608 is operating within its preset operational limit and, if not, to adjust a speed of the pump 608 to be within its preset operational limit and/or cause a user notification to be provided indicating a possible pump failure situation. For another example, the computer 602 receives fan rotation information from a fan tachometer coupled to the fan 618 to determine whether the fan is rotating above a predetermined threshold and, if so, to adjust a speed of the fan 618 to be within its preset operational limit and/or cause a user notification to be provided indicating a possible overheating situation.

In an exemplary embodiment, the computer 602 is configured to provide the user notification without causing any automatic corrective action to be performed in order to increase user control. In other embodiments, the computer 602 is configured to automatically cause a corrective action to be performed for certain conclusions drawn from received information, namely conclusions that pose an imminent risk to patient safety and/or control module failure, such as automatically reducing a speed of the pump 608 if it is determined to be running above its maximum safe limit or stopping the pump 608 if too many air bubbles are detected, and to not automatically cause a corrective action to be performed for all other conclusions drawn from received information.

Figure 22:
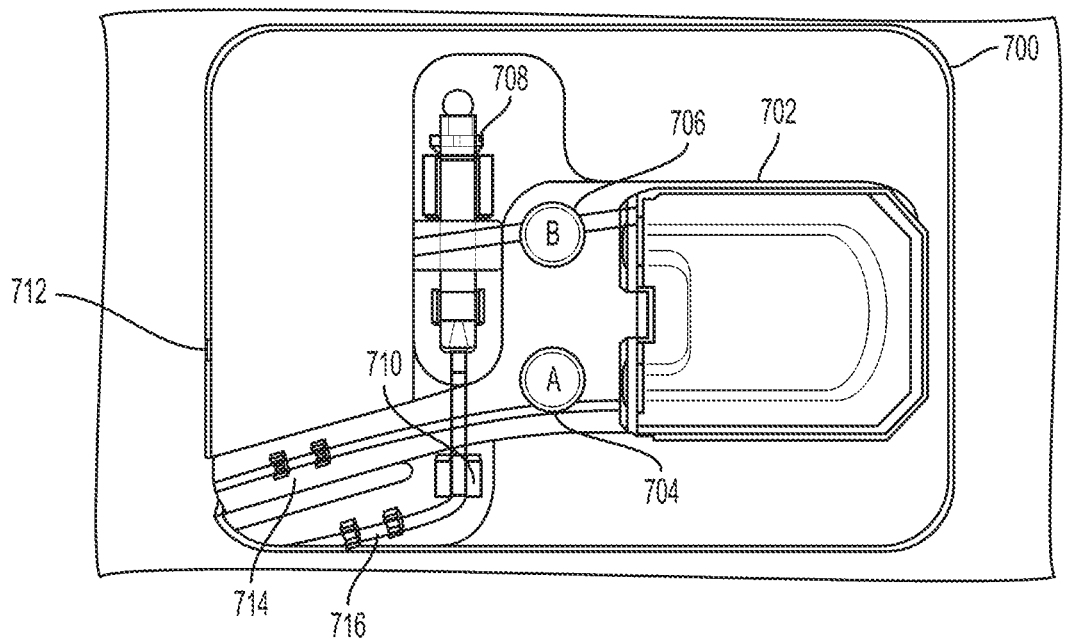
FIG. 22 is a front view of one embodiment of the control module of FIG. 21.

FIG. 22 illustrates one embodiment of the control module 600 of FIG. 21. The control module includes a housing 700 having electronic components disposed therein (e.g., the controller 604, the safety relays board 606, the alarm notification mechanism 616, the fan 618, the power supply 622, etc.). Attached to the housing 700 are a pump 702, pump pressure sensors that include a pump inlet pressure sensor 704 and a pump outlet pressure sensor 706, a drip chamber 708, an air bubble detector 710, a catheter pressure sensor inlet 712 configured to couple to the catheter pressure sensors, an inlet blood line clamp 714 configured to clamp to an inlet tube of a blood line through which blood flows from the patient to the pump 702, and an outlet blood line clamp 716 configured to couple to an outlet tube of the blood line through which blood flows from the pump 702 to the patient. The blood line can include any of a variety of tubing sets, as will be appreciated by a person skilled in the art. The control module of FIG. 22 does not include a computer and is configured to electronically couple to a computer.

A control module configured to control the operation of a system including a catheter can include one or more feedback loops to adjust performance of the system to create and maintain a low pressure zone while lymphatic fluid is cleared in a context of a system configured to treat pulmonary edema in a patient. FIGS. 23-28 illustrate one embodiment of a process to create a low pressure zone and transport fluid from a low pressure zone back into the venous system of a patient in a context of a system configured to treat pulmonary edema in a patient.

Figure 23:
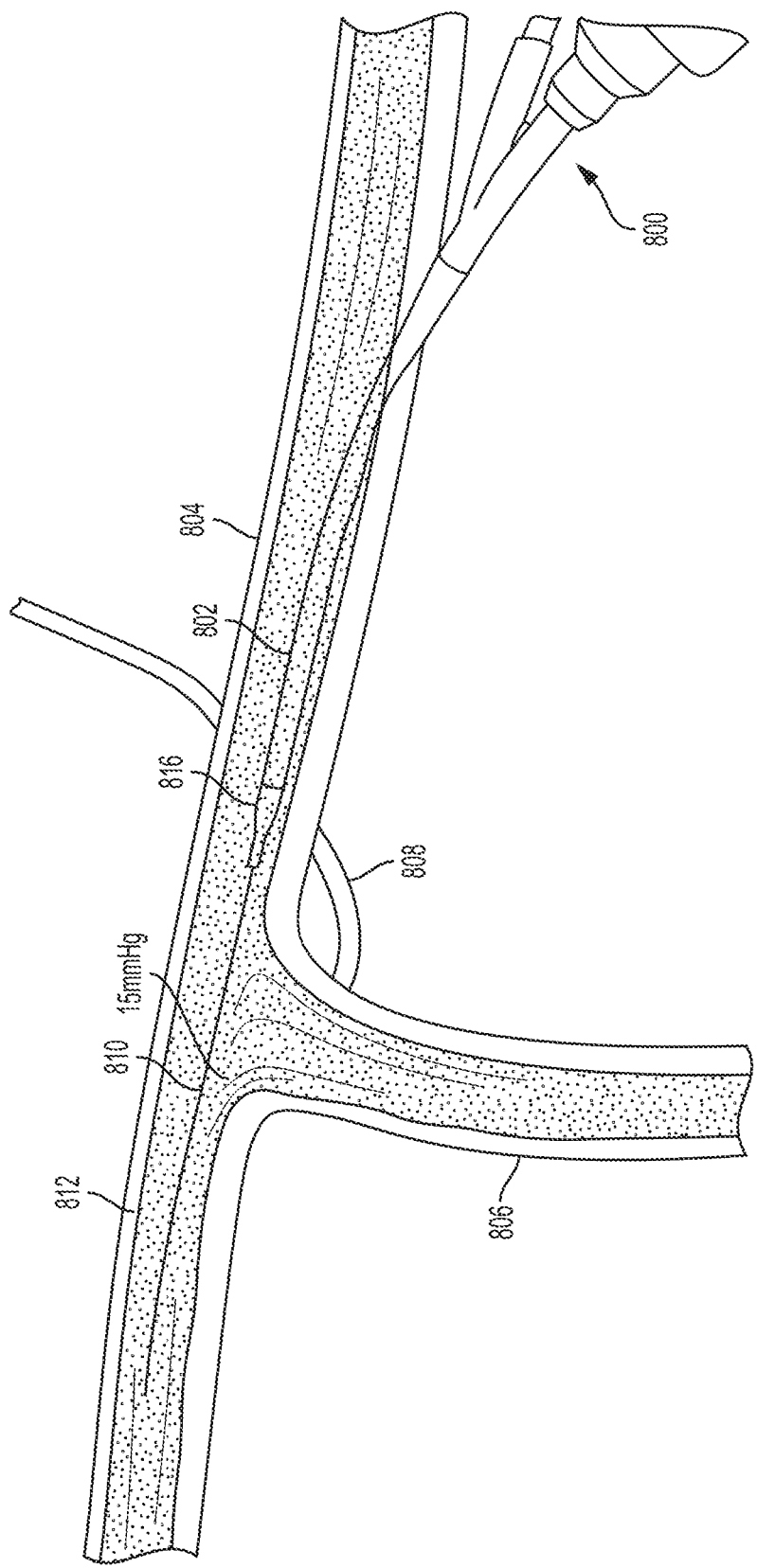
FIG. 23 is a perspective partially cross-sectional view of a distal portion of one embodiment of a catheter system advanced into a body of a patient.

As shown in FIG. 23, a distal portion of a catheter system 800 is introduced into a patient. A distal end of a sheath 802 is positioned within a jugular vein 804 of the patient proximal to a subclavian vein 806 of the patient and thoracic duct 808 outlet. A distal end of a catheter 814. e.g., an atraumatic distal tip 816 thereof, just beyond the distal end of the sheath 802 is also positioned within the jugular vein 804 proximal to the subclavian vein 806 and the thoracic duct 808 outlet. A guidewire 810 extending through the sheath 802 and the catheter 814 extends distally beyond the sheath's distal end and the catheter's distal end and extends distally past the subclavian and jugular bifurcation to be in an innominate vein 812 of the patient. Blood continues to flow normally from the jugular vein 804 into the innominate vein 812 and from the subclavian vein 806 into the innominate vein 812, with the blood flowing around the sheath 802 and catheter 814. A pressure at the subclavian and jugular bifurcation at this point is shown in FIG. 23 as being at 15 mmHg.

Figure 24:
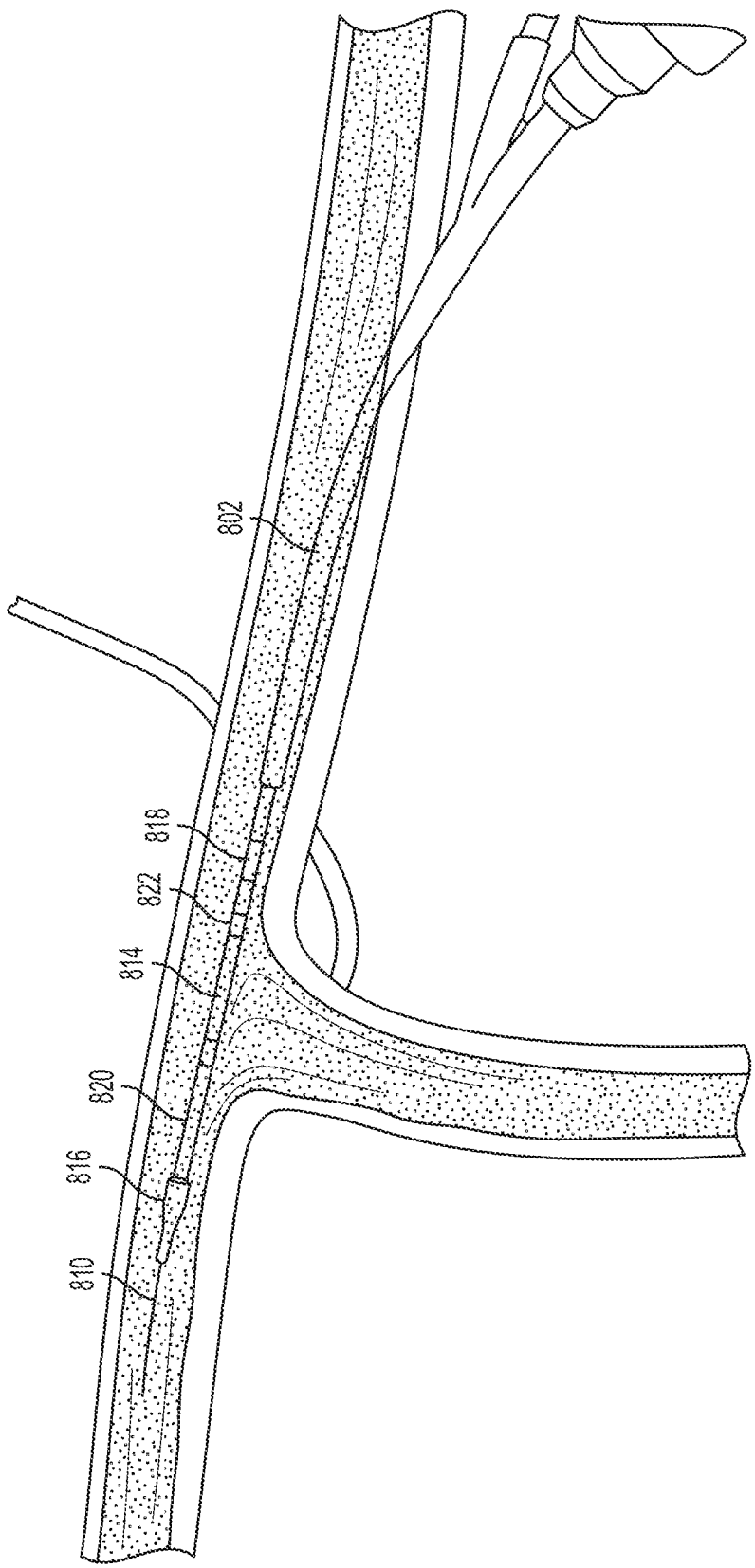
FIG. 24 is a perspective partially cross-sectional view of a catheter of the catheter system of FIG. 23 advanced distally out of a sheath of the catheter system with restrictors of the catheter being in a collapsed configuration.

As shown in FIG. 24, the catheter 814 is then advanced distally from the sheath 802 over the guidewire 810 to extend across the subclavian and jugular bifurcation. A proximal restrictor 818 of the catheter 814 is positioned proximal to (upstream of) the subclavian and jugular bifurcation, and hence proximal to the thoracic duct 808 outlet, and a distal restrictor 820 of the catheter 814 is positioned distal to (downstream) of the subclavian and jugular bifurcation, and hence distal to the thoracic duct 808 outlet. The proximal and distal restrictors 818, 820 are collapsed. A flexible membrane 822 of the catheter 814 is also collapsed. Blood continues to flow normally from the jugular vein 804 into the innominate vein 812 and from the subclavian vein 806 into the innominate vein 812, with the blood flowing around the sheath 802 and catheter 814.

Figure 25:
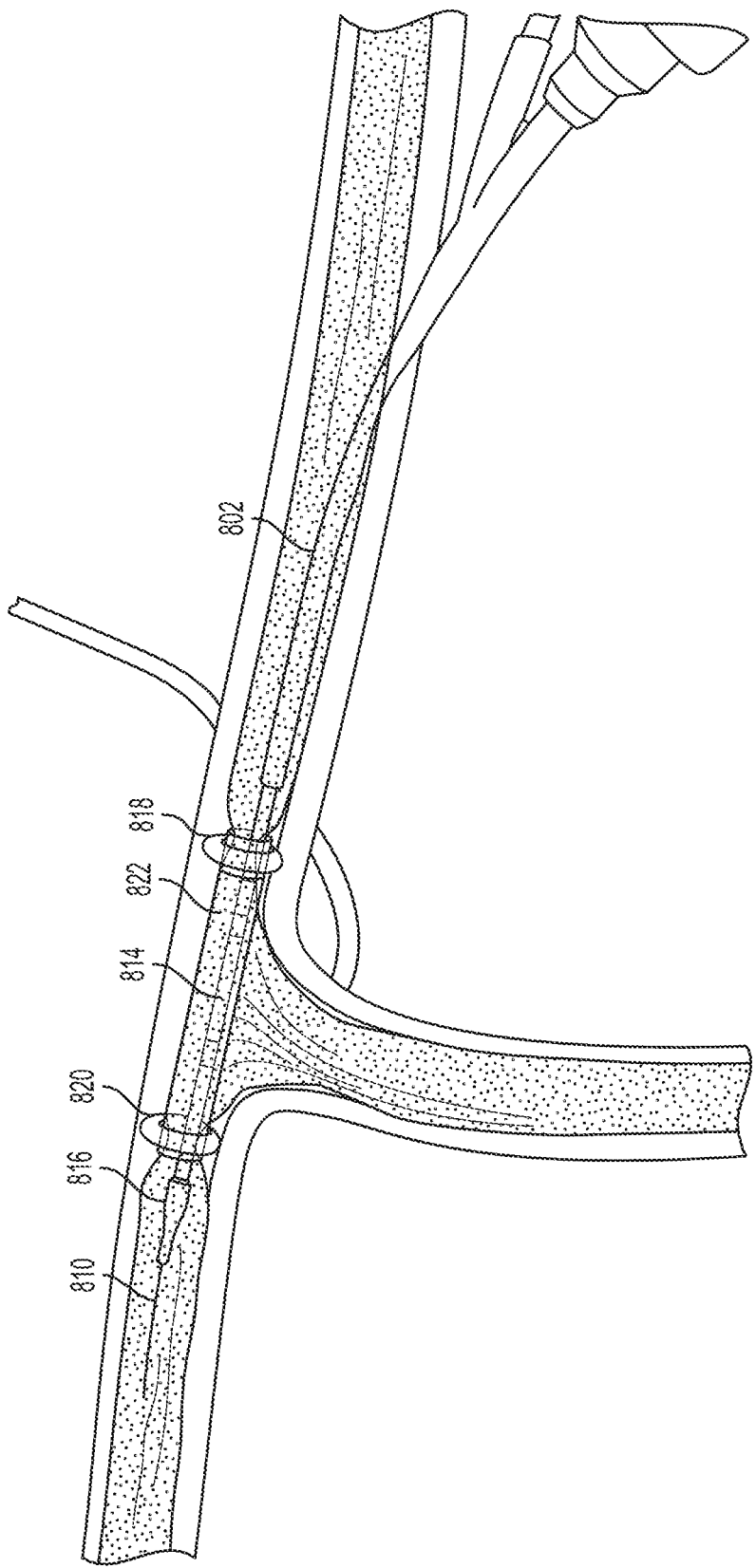
FIG. 25 is a perspective partially cross-sectional view of the sheath and catheter of FIG. 24 with the restrictors in an expanded configuration.

As shown in FIG. 25, the restrictors 818, 820 and the flexible membrane 822 are then expanded. Blood now flows from the jugular vein 804 into the flexible membrane 822 and flows therethrough across the subclavian and jugular bifurcation into the innominate vein 812. Blood is now not flowing from the subclavian vein 806 into the innominate vein 812.

Figure 26:
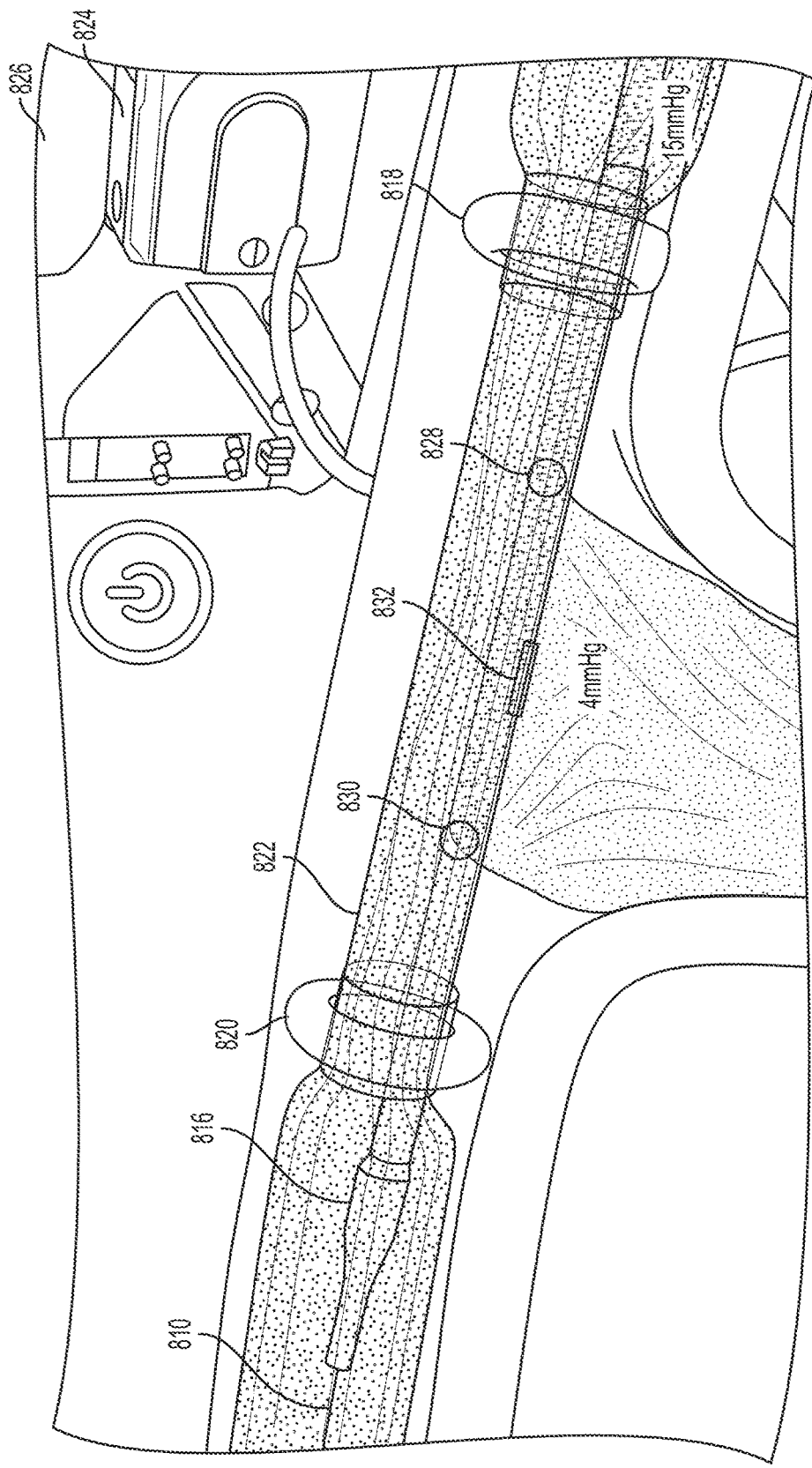
FIG. 26 is a perspective partially cross-sectional view of the catheter of FIG. 25 with a pump of the catheter system suctioning blood through the catheter.
Figure 26A:
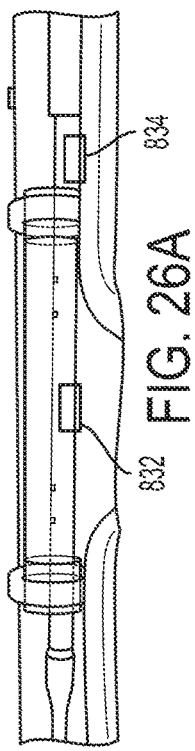
FIG. 26A is side partially cross-sectional view of the catheter of FIG. 26.

As shown in FIG. 26, a pump 824 of a control module 826 is activated (e.g., is turned on, as indicated by an illuminated power light shown standing alone in FIG. 26 to allow it to be visible in FIG. 26) to suction blood into proximal and distal suction ports 828, 830 of the catheter 814 that are located between the restrictors 818, 820. The suctioning draws the blood into the catheter 814 (e.g., into the catheter shaft's inner lumen) and toward the pump 824, and the suctioning reduces the pressure at the subclavian and jugular bifurcation. A pressure at the subclavian and jugular bifurcation at this point is shown in FIG. 26 as being at 4 mmHg, which is reduced from the previous 15 mmHg value at the subclavian and jugular bifurcation. The pressure is measured at the subclavian and jugular with a first pressure sensor 832 of the catheter 814. The pressure proximal to the proximal restrictor 818 is shown as 15 mmHg in FIG. 23. The pressure proximal to the proximal restrictor 818 is measured with a second pressure sensor 834 of the catheter 814 (see FIG. 26A). A low pressure zone has thus been formed between the restrictors 818, 820. Blood now flows from the jugular vein 804 into the flexible membrane 822 and flows therethrough across the subclavian and jugular bifurcation into the innominate vein 812. Blood now flows from the subclavian vein 806 into the catheter 814.

Figure 27:
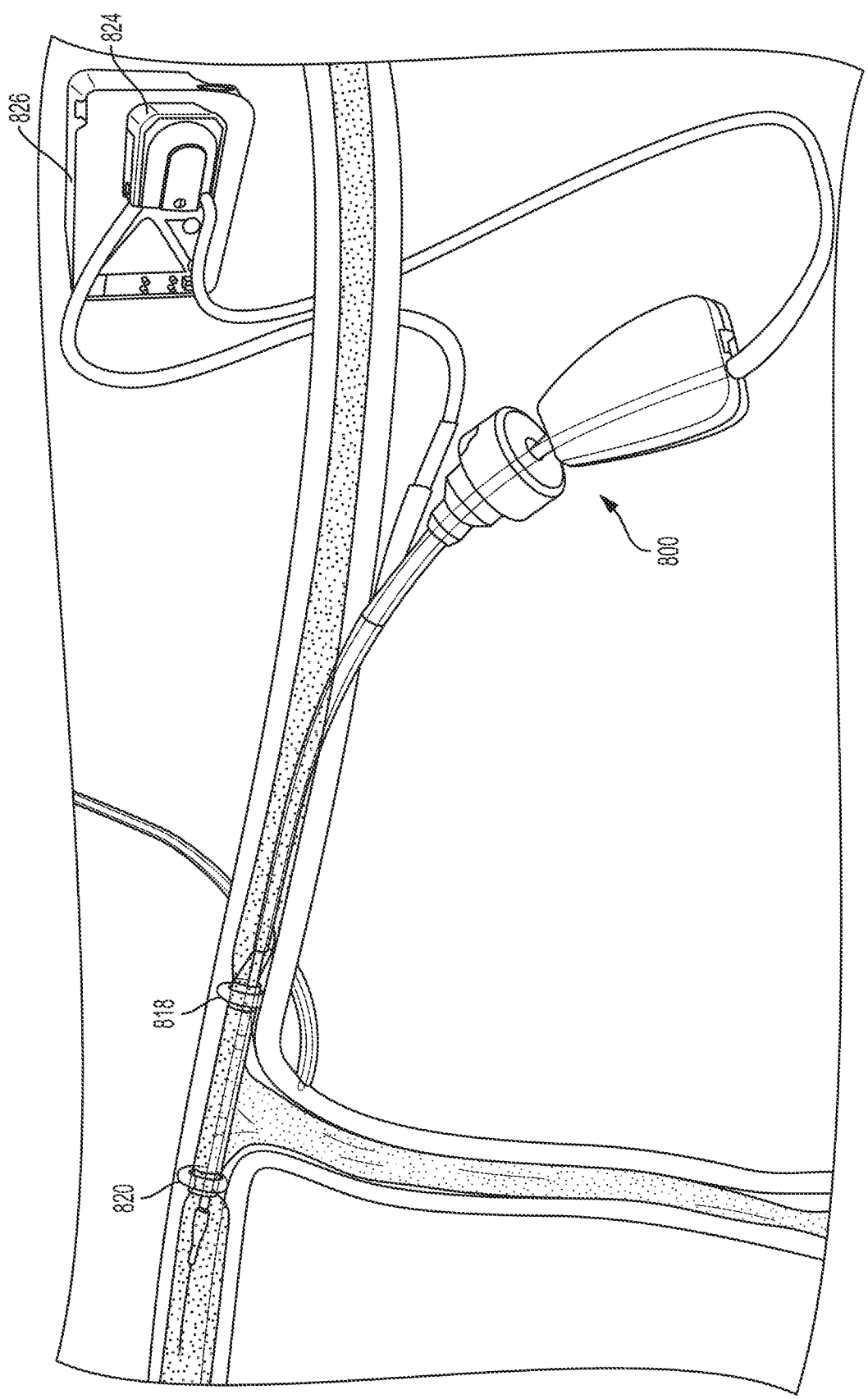
FIG. 27 is a perspective partially cross-sectional view of the catheter of FIG. 26 with the pump of the catheter system suctioning blood through the catheter and discharging blood into the sheath.
Figure 28:
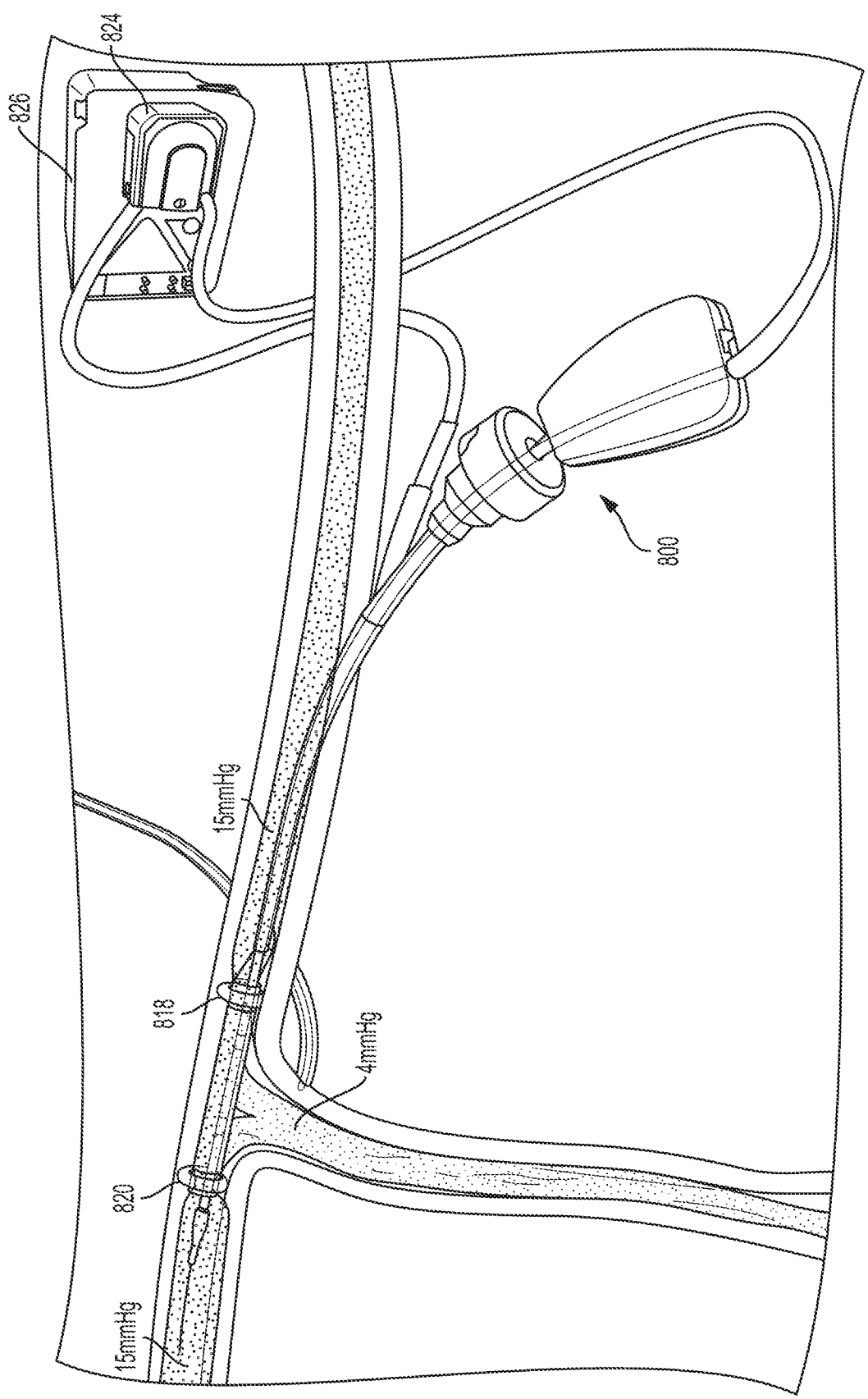
FIG. 28 is a perspective partially cross-sectional view of the catheter of FIG. 27.

As shown in FIG. 27, blood returns to the sheath 802 from the pump 824 to flow into the flexible membrane 822 proximal to the proximal restrictor 818 and across the subclavian and jugular bifurcation into the innominate vein 812. Blood now flows from the jugular vein 804 into the flexible membrane 822 and flows therethrough across the subclavian and jugular bifurcation into the innominate vein 812. Blood now flows from the subclavian vein 806 into the catheter 814 and returns to the patient via the sheath 802. FIG. 28 shows the low pressure zone with a pressure of 4 mmHg and pressures on either side thereof as being at 15 mmHg.

The blood flow of FIGS. 27 and 28 remains until the pump 824 is deactivated (e.g., turned off) and/or the restrictors 818, 820 are collapsed. The control module 826 functions as discussed herein, allowing data for various parameters to be collected and analyzed.

Figure 29:
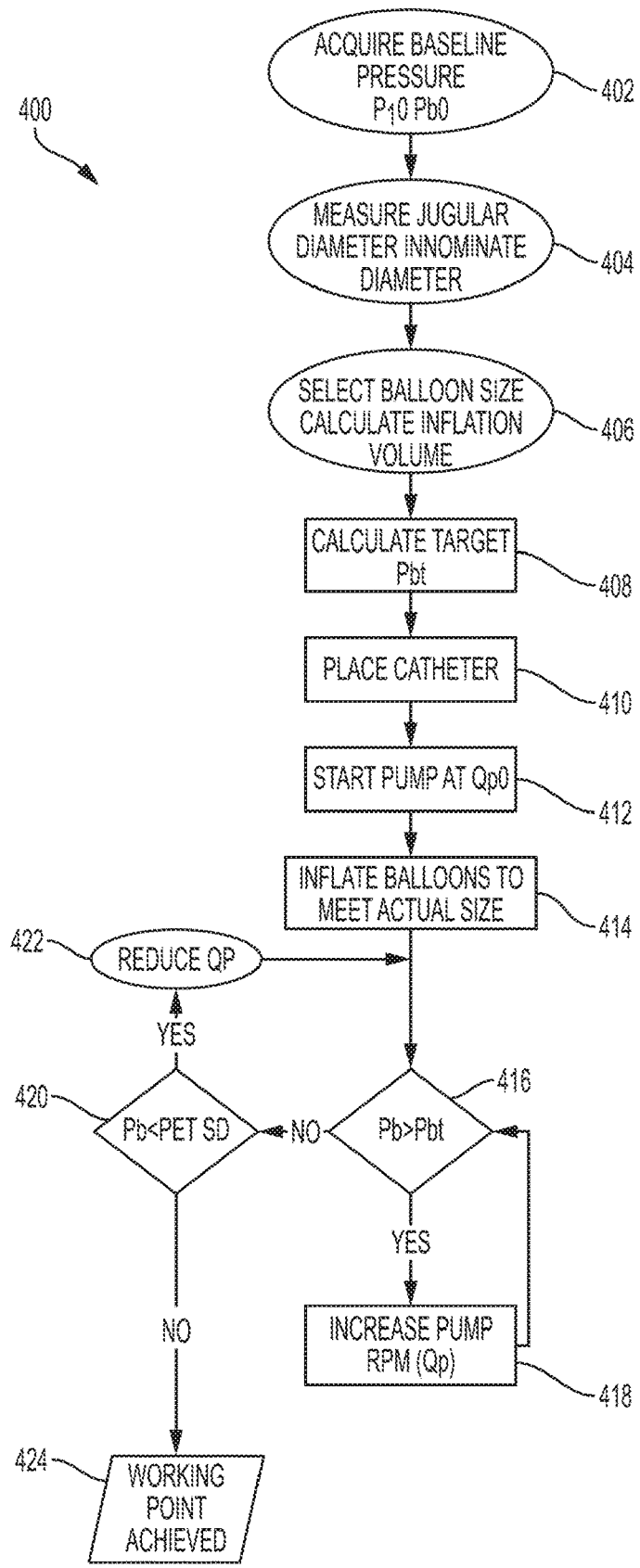
FIG. 29 is a flow diagram for one embodiment of operation of a control module for a system of treating edema.

FIG. 29 illustrates another embodiment of a process 400 to create a low pressure zone and transport fluid from a low pressure zone back into the venous system of a patient in a context of a system configured to treat pulmonary edema in a patient. At step 402 of the process 400 a control module acquires baseline pressure(s), such as a jugular pressure and a baseline bifurcation pressure. The baseline bifurcation pressure is acquired, for example, by the pressure sensors of a catheter of the system when the one or more pressure sensors are out of the system's sheath. Once the catheter is taken out of the sheath, the pressure sensors can read baseline pressure within the patient. After the baseline pressure is read, the catheter can be advanced to its final position within the patient.

The control module at step 404 of the process 400 measures a diameter of the patient's jugular vein and a diameter of the patient's innominate vein. The diameters can be measured, for example, by a correlation between a volume that is inflated into the catheter's restriction members and the pressure reading at the catheter's pressure sensors. When the distal one of the restriction members (e.g., the restriction member positioned in the patient's innominate vein) is inflated to the level of the vein in which it is positioned suddenly there is an abrupt increase pressure, which is read by the catheter's pressure sensors (e.g., one pressure sensor in the patient's jugular vein and another pressure sensor in the patient's innominate vein). This abrupt increase indicates that the vessel diameter has been achieved. From the amount of volume that was inflated, the diameters are now known since there exists a 1:1 correlation between the volume and diameter curve for the restriction members.

At step 406 of the process 400 the control module selects an inflation size of the system's restrictor(s) and can calculate a volume of the restrictor(s). In the distal one of the restriction members, the inflation size is measured as described above, for example. In the proximal one of the restriction members (e.g., the restriction member positioned in the patient's jugular vein), the inflation size is determined, for example, using a visualization technique such as ultrasound to measure the correct diameter, as it can be easily visualized. At step 408 of the process 400, a target bifurcation pressure is calculated by the control module. The target pressure is taken to be, for example, over 50% reduction from the baseline pressure.

At step 410 of the process 400, a catheter of the system is placed within the patient, for example by being distally advanced out of a sheath as discussed above. At step 412 of the process 400, a flow rate of a pump of the system equals zero, and a volume of each of the system's one or more restrictors equals zero. Next, at step 414 of the process 400, the control module causes the restriction member(s) to be deployed (e.g., inflated) to accommodate the vein size. The restriction member(s) are inflated to the inflation size selected above.

At step 416 of the process 400, the control module determines if the baseline bifurcation pressure (Pb) is greater than the target bifurcation pressure (Pbt). If the baseline bifurcation pressure is greater than the target bifurcation pressure, the control increases the pump flow at step 418 of the process 400. The process 400 then reverts back to repeat step 416 to re-measure the target bifurcation pressure. With two pressure sensors (in the innominate and jugular veins in this example) that work simultaneously, this process 400 is accurate and real time. If the baseline bifurcation pressure is not greater than the target bifurcation pressure, then the process 400 proceeds to step 420 in which the control module determines if the baseline bifurcation pressure is less than the target bifurcation pressure minus a safety delta (SD). The safety delta comes from different scenarios. The target bifurcation pressure is typically in a range of 0 to 5 mmHg. However, if the baseline pressure is very high (e.g., above about 15 mmHg) it can also be considered a successful treatment if the target pressure is above the typical range, e.g., is in a range of about 5 to 7 mmHg. Therefore, for each baseline pressure there is a target pressure which can be more than 50% of the baseline pressure. If the baseline bifurcation pressure is less than the target bifurcation pressure minus the safety delta, the process 400 proceeds to step 422 to reduce the initial pump flow, and the process 400 re-measures the target bifurcation pressure at step 416. If the baseline bifurcation pressure is not less than the target bifurcation pressure minus the safety delta, the process 400 advances to step 424 and a working system condition is achieved.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical system, comprising:
a catheter configured to be positioned within a vein of a patient;
an impeller attached to a distal portion of the catheter;
a selectively deployable restrictor coupled to the catheter, at least a portion of the selectively deployable restrictor disposed around an axis of the impeller; and
at least one inlet opening proximal to the selectively deployable restrictor, wherein, when the impeller is activated, the impeller facilitates suction of fluid into the at least one inlet opening.

2. The system of claim 1, wherein the restrictor includes a balloon.

3. The system of claim 2, further comprising at least one inflation lumen extending along the catheter, the at least one inflation lumen being in fluid communication with the restrictor.

4. The system of claim 1, wherein the restrictor is movable between an activated configuration in which the restrictor has a first diameter and a relaxed configuration in which the restrictor has a second diameter that is less than the first diameter.

5. The system of claim 1, further comprising a controller configured to actuate the impeller.

6. The system of claim 5, wherein the controller is configured to actuate the impeller in response to user operation of a control external to the body of the patient.

7. The system of claim 5, further comprising a pressure sensor configured to be implanted in the body of the patient, the controller being configured to actuate the impeller in response to a pressure measured by the pressure sensor exceeding a predefined threshold.

8. The system of claim 5, further comprising a pressure sensor configured to be implanted in the body of the patient, the controller being configured to control a speed of the impeller depending on a pressure measured by the pressure sensor.

9. The system of claim 1, wherein the vein includes an internal jugular vein, an innominate vein, or a subclavian vein.

10. A catheter for treating edema, the catheter comprising:
a catheter;
a proximal restrictor disposed around a portion of the catheter;
a distal restrictor coupled to a distal portion of the catheter;
at least one opening proximal to the distal restrictor;

an impeller attached to the distal portion of the catheter, wherein at least a portion of the distal restrictor is disposed around an axis of the impeller; and a drive shaft extending proximally from the impeller to a motor.

11. The catheter of claim 10, further comprising a distally-tapering atraumatic tip.

12. The catheter of claim 11, wherein the tip comprises a discharge opening.

13. The catheter of claim 10, wherein the motor is external to the extended catheter shaft.

14. The catheter of claim 10, further comprising a bearing proximal to the impeller to stabilize the impeller within the catheter.

15. A catheter for treating edema, the catheter comprising:

a catheter dimensioned for insertion into an internal jugular vein or a subclavian vein of a patient;

at least one proximal opening and at least one distal opening along a portion of the catheter;

an impeller operably connected to a motor via a drive shaft, the impeller located at least partially within a section of the catheter extending substantially between the proximal and distal inlet openings; and at least one selectively-deployable restrictor disposed about the section of the catheter, wherein at least a portion of one of the at least one selectively-deployable restrictor is disposed around an axis of the impeller.

* * * * *